US008350084B2

(12) United States Patent
Starrett, Jr. et al.

(10) Patent No.: US 8,350,084 B2
(45) Date of Patent: Jan. 8, 2013

(54) ALPHA-(N-SULFONAMIDO)ACETAMIDE COMPOUND AS AN INHIBITOR OF BETA AMYLOID PEPTIDE PRODUCTION

(75) Inventors: John E. Starrett, Jr., Middletown, CT (US); Kevin W. Gillman, Madison, CT (US); Richard E. Olson, Orange, CT (US); Lawrence R. Marcin, Bethany, CT (US); Bang-Chi Chen, Cranbury, NJ (US); Huiping Zhang, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/299,703

(22) Filed: Nov. 18, 2011

(65) Prior Publication Data

US 2012/0088925 A1 Apr. 12, 2012

Related U.S. Application Data

(63) Continuation of application No. 12/249,180, filed on Oct. 10, 2008, now Pat. No. 8,084,477.

(60) Provisional application No. 60/984,118, filed on Oct. 31, 2007.

(51) Int. Cl.
 *C07C 311/16* (2006.01)
(52) U.S. Cl. ....................................... 564/92
(58) Field of Classification Search ..................... None
See application file for complete search history.

(56) References Cited

U.S. PATENT DOCUMENTS

| | | | |
|---|---|---|---|
| 5,274,094 A | 12/1993 | Whittaker et al. |
| 5,516,783 A | 5/1996 | Whittaker et al. |
| 5,849,736 A | 12/1998 | Wityak et al. |
| 6,153,612 A | 11/2000 | Ortwine et al. |
| 6,313,123 B1 | 11/2001 | Levin et al. |
| 6,541,467 B1 | 4/2003 | Ho et al. |
| 7,144,894 B2 | 12/2006 | Gilligan |
| 7,300,936 B2 | 11/2007 | Parker et al. |
| 7,300,951 B2 | 11/2007 | Kreft et al. |
| 7,687,666 B2 | 3/2010 | Chan et al. |
| 7,786,122 B2 | 8/2010 | Parker et al. |
| 7,838,550 B2 | 11/2010 | Chan et al. |
| 8,044,077 B2 | 10/2011 | Starrett, Jr. et al. |
| 2009/0227642 A1 | 9/2009 | Starrett, Jr. et al. |

FOREIGN PATENT DOCUMENTS

| | | |
|---|---|---|
| JP | 11-343279 | 12/1999 |
| WO | WO 98/03166 | 1/1998 |
| WO | WO 00/44716 | 8/2000 |
| WO | WO 00/50391 | 8/2000 |
| WO | WO 03/072576 A2 | 9/2003 |
| WO | WO 2008/112249 | 9/2008 |
| WO | WO 2009/005688 | 1/2009 |

OTHER PUBLICATIONS

Konosu, T., et al, "Synthesis and in Vitro Antifungal Activities of Novel Triazole Antifungal Agent CS-758," Chemical & Pharmaceutical Bulletin, vol. 49 (12), pp. 1647-1650, 2001 (XP001248164).

Chapman, P.F. et al., "Impaired synaptic plasticity and learning in aged amyloid precursor protein transgenic mice", Nature Neuroscience, vol. 2, No. 3, pp. 271-276 (1999).
Dahlgren, K.N. et al., "Oligomeric and Fibrillar Species of Amyloid-β. Peptides Differentially Affect Neuronal Viability", The Journal of Biological Chemistry, vol. 277, No. 35, pp. 32046-32053 (2002).
Golde, T.E., "Alzheimer's disease therapy: Can the amyloid cascade be halted?", The Journal of Clinical Investigation, vol. 111, No. 1, pp. 11-18 (2003).
Götz, J. et al., "Formation of Neurofibrillary Tangles in P301L Tau Transgenic Mice Induced by Aβ42 Fibrils", Science, vol. 293, pp. 1491-1495 (2001).
Lewis, J. et al., "Enhanced Neurofibrillary Degeneration in Transgenic Mice Expressing Mutant Tau and APP", Science, vol. 293, pp. 1487-1491 (2001).
Loane, D.J. et al., "Amyloid precursor protein secretases as therapeutic targets for traumatic brain injury", Nature Medicine, Advance Online Publication, pp. 1-3 (Mar. 15, 2009).
Mayer, S.C. et al., Discovery of Begacestat, a Notch-1-Sparing γ-Secretase Inhibitor for the Treatment of Alzheimer's Disease, Journal of Medicinal Chemistry, vol. 51, No. 23, pp. 7348-7351 (2008).
McLean, C.A. et al., "Soluble Pool of Aβ Amyloid as a Determinant of Severity of Neurodegeneration in Alzheimer's Disease", Annals of Neurology, vol. 46, No. 6, pp. 860-866 (1999).
Seiffert, D. et al., "Presenilin-1 and -2 are Molecular Targets for γ-Secretase Inhibitors", The Journal of Biological Chemistry, vol. 275, No. 44, pp. 34086-34091 (2000).
Selkoe, D.J., "Alzheimer's Disease: Genes, Proteins, and Therapy", Physiological' Reviews, vol. 81, No. 2, pp. 741-766 (2001).
Selkoe, D.J., "Cell Biology of the Amyloid β-Protein Precursor and the Mechanism of Alzheimer's Disease", Ann. Rev. Cell Biol., vol. 10, pp. 373-403 (1994).
Siemers, E.R. et al., "Effects of a γ-secretase inhibitor in a randomized study of patients with Alzheimer disease", Neurology, vol. 66, pp. 602-604 (2006).
Thal, D.R. et al., "Two Types of Sporadic Cerebral Amyloid Angiopathy", Journal of Neuropathology and Experimental Neurology, vol. 61, No. 3, pp. 282-293 (2002).
Walsh, D.M. et al., "Naturally secreted oligomers of amyloid β protein potently inhibit hippocampal long-term potentiation in vivo", Nature, vol. 416, pp. 535-539 (2002).
Watkins, T.A. et al., "Distinct Stages of Myelination Regulated by β-Secretase and Astrocytes in a Rapidly Myelinating CNS Coculture System", Neuron, vol. 60, pp. 555-569 (2008).
Wolfe, M.S., "Secretase Targets for Alzheimer's Disease: Identification and Therapeutic Potential", Journal of Medicinal Chemistry, vol. 44, No. 13, pp. 2039-2060 (2001).

(Continued)

*Primary Examiner* — Kamal Saeed
(74) *Attorney, Agent, or Firm* — Pamela A. Mingo; Aldo A. Algieri

(57) ABSTRACT

The present invention provides a novel alpha-(N-sulfonamido)acetamide compound, its pharmaceutical composition, processes thereof and a method for the treatment of Alzheimer's disease and other conditions associated with β-amyloid peptide.

1 Claim, No Drawings

OTHER PUBLICATIONS

2008 CSHL Meeting on Neurodegenerative Diseases, Oral Presentation, Dec. 5, 2008.
2009 BMS URG Symposium, Oral Presentation, May 1, 2009.
237th National American Chemical Society Meeting, Salt Lake City, Utah, Oral Presentation, Mar. 22, 2009.
Gordon Research Conference, Newport, RI, Oral Presentation, Jun. 30, 2009.
International Conference on Alzheimer's Disease, Chicago, IL, Abstract, Jul. 26, 2008.
International Conference on Alzheimer's Disease, Chicago, IL, Oral Presentation, Jul. 30, 2008.

ALPHA-(N-SULFONAMIDO)ACETAMIDE COMPOUND AS AN INHIBITOR OF BETA AMYLOID PEPTIDE PRODUCTION

REFERENCE TO RELATED APPLICATIONS

This application is a Continuation of U.S. Non-Provisional application Ser. No. 12/249,180 filed Oct. 10, 2008 which claims the benefit of U.S. Provisional Application Ser. No. 60/984,118 filed Oct. 31, 2007.

FIELD OF THE INVENTION

The present invention relates to (2R)-2-[[(4-chlorophenyl)sulfonyl][[2-fluoro-4-(1,2,4-oxadiazol-3-yl)phenyl]methyl]amino]-5,5,5-trifluoropentanamide having drug and bio-affecting properties, its pharmaceutical compositions, processes thereof and methods of use. The novel compound possesses a unique inhibition of Aβ peptide production, thereby acting to prevent the accumulation of Aβ peptides and/or amyloid protein deposits in the brain, and is useful in the treatment or delaying the onset of Alzheimer's disease (AD), Down syndrome, mild cognitive impairment and other conditions associated with β-amyloid peptide.

BACKGROUND

Alzheimer's disease (AD) is a progressive neurodegenerative disease which begins with memory loss and progresses to include severe cognitive impairment, altered behavior, and decreased motor function (Grundman, M. et al., *Arch Neurol.* (2004) 61: 59-66; Walsh, D. M. et al., *Neuron* (2004) 44: 181-193). It is the most common form of dementia and represents the third leading cause of death after cardiovascular disorders and cancer. The cost of AD is enormous and includes the suffering of the patients and families and the lost productivity of patients and caregivers. No treatment that effectively prevents AD or reverses the clinical symptoms and underlying pathophysiology is currently available.

A definitive diagnosis of AD for a demented patient requires a histopathological evaluation of the number and localization of neuritic plaques and neurofibrillary tangles upon autopsy (Consensus recommendations for the postmortem diagnosis of Alzheimer's disease. *Neurobiol Aging* (1997) 18: S1-2). Similar alterations are observed in patients with Trisomy 21 (Down syndrome). Plaques primarily consist of β-amyloid (Aβ) peptides that are formed by a stepwise proteolytic cleavage of the amyloid precursor protein (APP) by β-site APP-cleaving enzyme (RACE), to generate the N-terminus, and γ-secretase, to generate the C-terminus (Selkoe, D. J., *Physiol Rev.* (2001) 81: 741-766). γ-Secretase is a transmembrane protein complex that includes Nicastrin, Aph-1, PEN-2, and either Presenilin-1 (PS-1) or Presenilin-2 (PS-2) (Wolfe, M. S. et al., *Science* (2004) 305: 1119-1123). PS-1 and PS-2 are believed to contain the catalytic sites of γ-secretase.

Aβ40 is the most abundant form of Aβ synthesized (80-90%), while Aβ42 is most closely linked with AD pathogenesis. In particular, mutations in the APP, PS-1, and PS-2 genes that lead to rare, familial forms of AD implicate Aβ42 aggregates as the primary toxic species (Selkoe, D. J., *Physiol Rev.*, (2001) 81: 741-766). Current evidence suggests that oligomeric, protofibrillar and intracellular Aβ42 play a significant role in the disease process (Cleary, J. P. et al., *Nat. Neurosci.* (2005) 8: 79-84). Inhibitors of the enzymes that form Aβ42, such as γ-secretase, represent potential disease-modifying therapeutics for the treatment of AD.

γ-Secretase cleaves multiple type I transmembrane proteins in addition to APP (Pollack, S. J. et al., *Curr Opin Investig Drugs* (2005) 6: 35-47). While the physiological significance of most of these cleavage events is unknown, genetic evidence indicates that γ-secretase cleavage of Notch is required for Notch signaling (Artavanis-Tsakonas, S. et al., *Science* (1999) 284 (5415): 770-6; Kadesch, T.; *Exp Cell Res.* (2000) 260(1): 1-8). In rodents dosed with γ-secretase inhibitors, drug-related toxicity has been identified in the gastrointestinal (GI) tract, thymus, and spleen (Searfoss, G. H.; Jordan et al., *J Biol. Chem.* (2003) 278: 46107-46116; Wong, G. T. et al., *J Biol. Chem.* (2004) 279: 12876-12882; Milano, J. et al., *Toxicol Sci.* (2004) 82: 341-358). These toxicities are likely linked to inhibition of Notch signaling (Jensen, J. et al., *Nat. Genet.* (2000) 24: 36-44).

The identification of mechanism-based toxicity raises the question of whether an acceptable therapeutic index can be achieved with γ-secretase inhibitors. Selective inhibition of Aβ formation over Notch processing, pharmacokinetics, drug disposition and/or tissue-specific pharmacodynamics could impact therapeutic margin.

Evidence suggests that a reduction in brain Aβ levels by inhibition of γ-secretase may prevent the onset and progression of AD (Selkoe, D. *Physiol. Rev.* (2001) 81: 741-766; Wolfe, M., *J. Med. Chem.* (2001) 44: 2039-2060). There are emerging data for the role of Aβ in other diseases, including mild cognitive impairment (MCI), Down syndrome, cerebral amyloid angiopathy (CAA), dementia with Lewy bodies (DLB), amyotrophic lateral sclerosis (ALS-D), inclusion body myositis (IBM), and age-related macular degeneration. Advantageously, compounds that inhibit γ-secretase and reduce production of Aβ could be used to treat these or other Aβ-dependent diseases.

Excess production and/or reduced clearance of Aβ causes CAA (Thal, D. et al., *J. Neuropath. Exp. Neuro.* (2002) 61: 282-293). In these patients, vascular amyloid deposits cause degeneration of vessel walls and aneurysms that may be responsible for 10-15% of hemorrhagic strokes in elderly patients. As in AD, mutations in the gene encoding Aβ lead to an early onset form of CAA, referred to as cerebral hemorrhage with amyloidosis of the Dutch type, and mice expressing this mutant protein develop CAA that is similar to patients. Compounds that specifically target γ-secretase could reduce or prevent CAA.

DLB manifests with visual hallucinations, delusions, and parkinsonism. Interestingly, familial AD mutations that cause Aβ deposits can also cause Lewy bodies and DLB symptoms (Yokota, O. et al., *Acta Neuropathol (Berl)* (2002) 104: 637-648). Further, sporadic DLB patients have Aβ deposits similar to those in AD (Deramecourt, V. et al., *J Neuropathol Exp Neurol* (2006) 65: 278-288). Based on this data, Aβ likely drives Lewy body pathology in DLB and, therefore, γ-secretase inhibitors could reduce or prevent DLB.

Approximately 25% of ALS patients have significant dementia or aphasia (Hamilton, R. L. et al., *Acta Neuropathol (Berl)* (2004) 107: 515-522). The majority (~60%) of these patients, designated ALS-D, contain ubiquitin-positive inclusions comprised primarily of the TDP-43 protein (Neumann, M. et al., *Science* (2006) 314: 130-133). About 30% of the ALS-D patients have amyloid plaques consistent with Aβ causing their dementia (Hamilton, R. L. et al., *Acta Neuropathol (Berl)* (2004) 107: 515-522). These patients should be identifiable with amyloid imaging agents and potentially treatable with γ-secretase inhibitors.

IBM is a rare, age-related degenerative disease of skeletal muscle. The appearance of Aβ deposits in IBM muscle and the recapitulation of several aspects of the disease by directing APP overexpression to muscle in transgenic mice support the role of Aβ in IBM (reviewed in Murphy, M. P. et al., *Neurology* (2006) 66: S65-68). Compounds that specifically target γ-secretase could reduce or prevent IBM.

In age-related macular degeneration, Aβ was identified as one of several components of drusen, extracellular deposits beneath the retinal pigment epithelium (RPE) (Anderson, D. H. et al., *Exp Eye Res* (2004) 78: 243-256). A recent study has shown potential links between Aβ and macular degeneration in mice (Yoshida, T. et al., *J Clin Invest* (2005) 115: 2793-2800). Increases in Aβ deposition and supranuclear cataracts have been found in AD patients (Goldstein, L. E. et al., *Lancet* (2003) 361: 1258-1265). Compounds that specifically target γ-secretase could reduce or prevent age-related macular degeneration.

Based on the role of Notch signaling in tumorigenesis, compounds which inhibit γ-secretase may also be useful as therapeutic agents for the treatment of cancer (Shih, I.-M., et al., *Cancer Research* (2007) 67: 1879-1882).

Smith, et al. in International Application WO 00/50391, published Aug. 31, 2000, disclose a series of sulfonamide compounds that can act to modulate production of amyloid β protein as a means of treating a variety of diseases, especially Alzheimer's disease and other diseases relating to the deposition of amyloid.

Japanese Patent No. 11343279, published Dec. 14, 1999 discloses a series of sulfonamide derivatives which are TNF-alpha inhibitors useful for treating autoimmune diseases.

Parker, et al. in International Application WO 03/053912, published Jul. 3, 2003, disclose a series of α-(N-sulphonamido)acetamide derivatives as β-amyloid inhibitors which are useful for the treatment of Alzheimer's disease and other conditions associated with β-amyloid peptide.

The novel compound of the present invention which falls within the definition of the Formula in WO 03/053912 is not disclosed or described by Parker, et al. Surprisingly, it has been discovered that (2R)-2-[[(4-chlorophenyl)sulfonyl][[2-fluoro-4-(1,2,4-oxadiazol-3-yl)phenyl]methyl]amino]-5,5,5-trifluoropentanamide possesses unique attributes which make it useful for the treatment of Alzheimer's disease and other conditions associated with β-amyloid peptide.

DESCRIPTION OF THE INVENTION

The present invention relates to (2R)-2-[[4-chlorophenyl)sulfonyl][[2-fluoro-4-(1,2,4-oxadiazol-3-yl)phenyl]methyl]amino]-5,5,5-trifluoropentanamide having the Formula I, its pharmaceutical formulations, and its use in inhibiting Aβ production in patients suffering from or susceptible to Alzheimer's disease (AD) or other disorders associated with β-amyloid peptide.

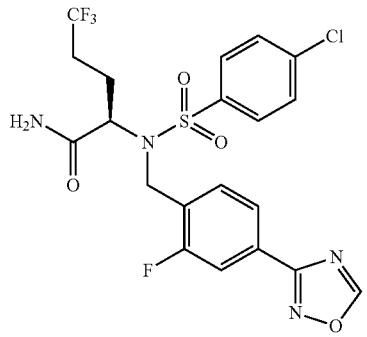

I

In another embodiment, the present invention provides a pharmaceutical composition comprising a therapeutically effective amount of (2R)-2-[[(4-chlorophenyl)sulfonyl][[2-fluoro-4-(1,2,4-oxadiazol-3-yl)phenyl]methyl]amino]-5,5,5-trifluoropentanamide in association with a pharmaceutically acceptable adjuvant, carrier or diluent.

In yet another embodiment, the present invention provides a method for the treatment, alleviation or delaying the onset of disorders associated with β-amyloid peptide, especially Alzheimer's disease, cerebral amyloid angiopathy, mild cognitive impairment, and Down syndrome which comprises administering together with a conventional adjuvant, carrier or diluent a therapeutically effective amount of (2R)-2-[[(4-chlorophenyl)sulfonyl][[2-fluoro-4-(1,2,4-oxadiazol-3-yl)phenyl]methyl]amino]-5,5,5-trifluoropentanamide or solvate or hydrate thereof.

In another aspect, the present invention provides a process for the preparation of (2R)-2-[[(4-chlorophenyl)sulfonyl][[2-fluoro-4-(1,2,4-oxadiazol-3-yl)phenyl]methyl]amino]-5,5,5-trifluoropentanamide comprising the step of reacting (R)-2-(4-chlorophenylsulfonamido)-5,5,5-trifluoropentanamide with 3-(4-(bromomethyl)-3-fluorophenyl)-1,2,4-oxadiazole in an inert organic solvent in the presence of a base and preferably an inorganic base such as cesium carbonate.

In still another aspect, the present invention provides a process for the preparation of (2R)-2-[[(4-chlorophenyl)sulfonyl][[2-fluoro-4-(1,2,4-oxadiazol-3-yl)phenyl]methyl]amino]-5,5,5-trifluoropentanamide comprising the steps of:
(a) reacting (R)-2-(4-chloro-N-(4-cyano-2-fluorobenzyl)phenylsulfonamido)-5,5,5-trifluoropentanamide with hydroxylamine, and
(b) treating the resulting (R)-2-(4-chloro-N-(2-fluoro-4-(M-hydroxycarbamimidoyl)benzyl)phenylsulfonamido)-5,5,5-trifluoropentanamide with triethyl orthoformate in an inert organic solvent in the presence of an acid catalyst.

As the compound of the present invention possesses an asymmetric carbon atom, the present invention includes the racemate as well as the individual enantiometric forms of the compound of Formula I and chiral and racemic intermediates as described herein. The use of a single designation such as (R) or (S) is intended to include mostly one stereoisomer. Mixtures of isomers can be separated into individual isomers according to known methods, e.g. fractional crystallization, adsorption chromatography or other suitable separation processes. Resulting racemates can be separated into antipodes in the usual manner after introduction of suitable salt-forming groupings, e.g. by forming a mixture of diastereosiomeric salts with optically active salt-forming agents, separating the mixture into diastereomeric salts and converting the separated salts into the free compounds. The enantiomeric forms may also be separated by fractionation through chiral high pressure liquid chromatography columns.

In the method of the present invention, the term "therapeutically effective amount" means the total amount of each active component of the method that is sufficient to show a meaningful patient benefit, i.e., healing of conditions associated with β-amyloid peptide. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing, delaying, suppressing or ameliorating diseases associated with β-amyloid peptide.

In still yet another embodiment of the invention, the compound of Formula I may be used in combination with other drugs that are used in the treatment/prevention/suppression or amelioration of the diseases or conditions for which the compound of Formula I is useful. Such other drugs may be administered by a route and in an amount commonly used therefor, contemporaneously or sequentially with the compound of the present invention. When the compound of Formula I is used contemporaneously with one or more other drugs, a pharmaceutical composition containing such drugs in addition to the compound of Formula I is preferred. Accordingly, the pharmaceutical compositions of the present invention include those that also contain one or more other active ingredients, in addition to the compound of Formula I. Examples of other active ingredients that may be combined with (2R)-2-[[(4-chlorophenyl)sulfonyl][[2-fluoro-4-(1,2,4-oxadiazol-3-yl) phenyl]methyl]amino]-5,5,5-trifluoropentanamide, either administered separately or in the same pharmaceutical compositions, to treat Alzheimer's disease include, but are not limited to: the class of drugs which are cholinesterase inhibitors, for example donepezil (Aricept®), rivastigmine (Exelon®), galantamine (Reminyl®, now Razadyne®); other drugs which are NMDA antagonists such as memantine (Namenda®) and PDE4 inhibitors such as cilomilast (Ariflo®); the class of NSAIDs, such as R-flurbiprofen (Flurizan®); the cholesterol-lowering statin drugs such as pravastatin, simvastatin, and atorvastatin; anti-amyloid and anti-Aβ immune therapy; compounds which inhibit the aggregation of Aβ, such as scylloinositol and clioquinol; other compounds which inhibit or modify Aβ production or processing such as γ-secretase inhibitors, β-secretase inhibitors, γ-secretase modulators, Aβ modulators, and GSK-3 inhibitors; compounds which regulate Aβ turnover such as PAI-1 inhibitors; compounds which regulate tau phosphorylation such as GSK-3 and CDK-5 inhibitors; PPAR$_γ$ agonists such as rosiglitazone; compounds which regulate tau or phosphor-tau turnover, or oligomerization such as HSP90 inhibitors, HDAC inhibitors and anti-tau immune therapy; and compounds which stabilize or bind to microtubules, such as taxane derivatives and epothilone derivatives; and compounds which regulate mitochondria function such as Dimebon.

In the treatment of cancer, the compound of the present invention may be used with known anti-cancer agents or treatments. Such agents and treatments include cytotoxic/cytostatic agents, androgen receptor modulators, estrogen receptor modulators, retinoid receptor modulators, prenyl-protein transferase inhibitors, angiogenesis inhibitors, agents that interfere with cell-cycle checkpoints, and radiation therapy. In addition, the compounds of the present invention may be useful in the treatment of immunological disorders such as Lupus.

The above therapeutic agents, when employed in combination with the compound of the present invention, may be used, for example, in those amounts indicated in the Physician's Desk Reference (PDR), where applicable or as otherwise determined by one of ordinary skill in the art.

However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms.

General Reaction Schemes

The compound of the present invention can be prepared in a number of different ways well-known to one skilled in the art of organic synthesis. The compound of Formula I can be prepared by the methods described below in Reaction Schemes 1-5. Reasonable variations of the described procedures, together with synthetic methods which would be evident to one skilled in the art, are intended to be within the scope of the present invention.

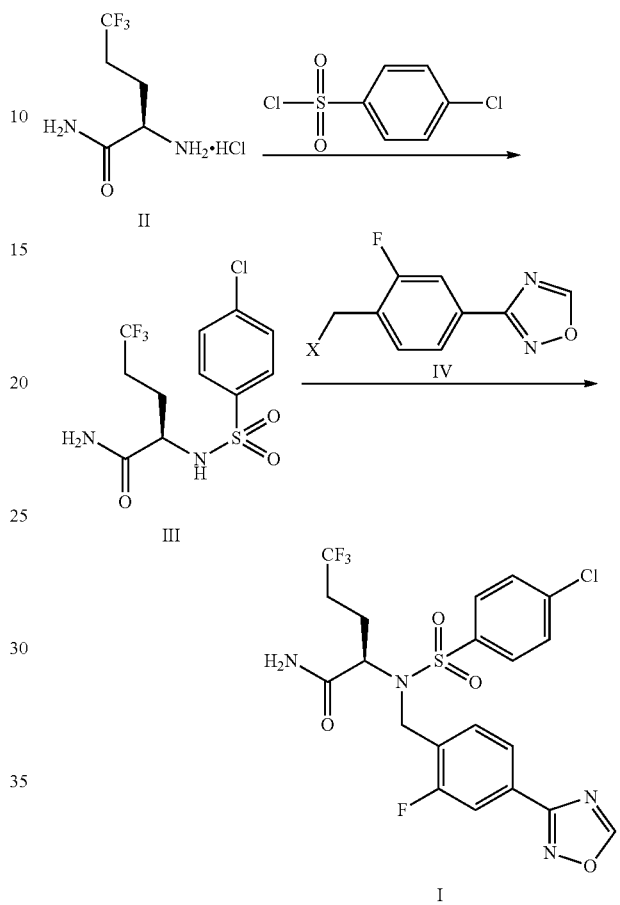

In one method of preparation illustrated in Reaction Scheme 1, the starting (α-amino)acetamide of Formula II which is used in substantially enantiomerically pure form may be prepared by well-known literature procedures such as using the asymmetric Strecker synthesis method described in Reaction Scheme 3 for the conversion of trifluorobutyraldehyde to the (α-amino)acetamide of Formula II, or alternatively from (R)-5,5,5-trifluoronorvaline (see; I. Ojima, *J. Org. Chem*. (1989) 54: 4511-4522) and the method described in Reaction Scheme 4 followed by the general procedures for amide preparation: R. C. Larock "Comprehensive Organic Transformations, VCH Publishers, New York, 1989, pp. 972-976. The (α-amino)acetamide of Formula II is treated with a suitable base and sulfonylated with p-chlorosulphonyl chloride in a suitable aprotic solvent such as CH$_2$Cl$_2$ at about room temperature to afford the (α-sulfonamido)acetamide of Formula III. Suitable bases include triethylamine, diisopropylamine, pyridine and the like.

The conversion of the compound of Formula III to the sulfonamide of Formula I is carried out in the presence of a base by reacting the (α-sulfonamido)acetamide of Formula III with an oxadiazole fluorobenzyl alkylating agent of Formula IV in a suitable aprotic solvent with or without heating. The fluorobenzyl oxadiazole of Formula IV may readily be prepared by methods well-known in the art wherein X is a leaving group and by the method described in Reaction Scheme 6. Suitable bases for this alkylation include inorganic bases such as potassium carbonate and cesium carbonate. Preferred solvents include DMF and acetonitrile. The temperature range for the reaction is typically 20° C. to 100° C.

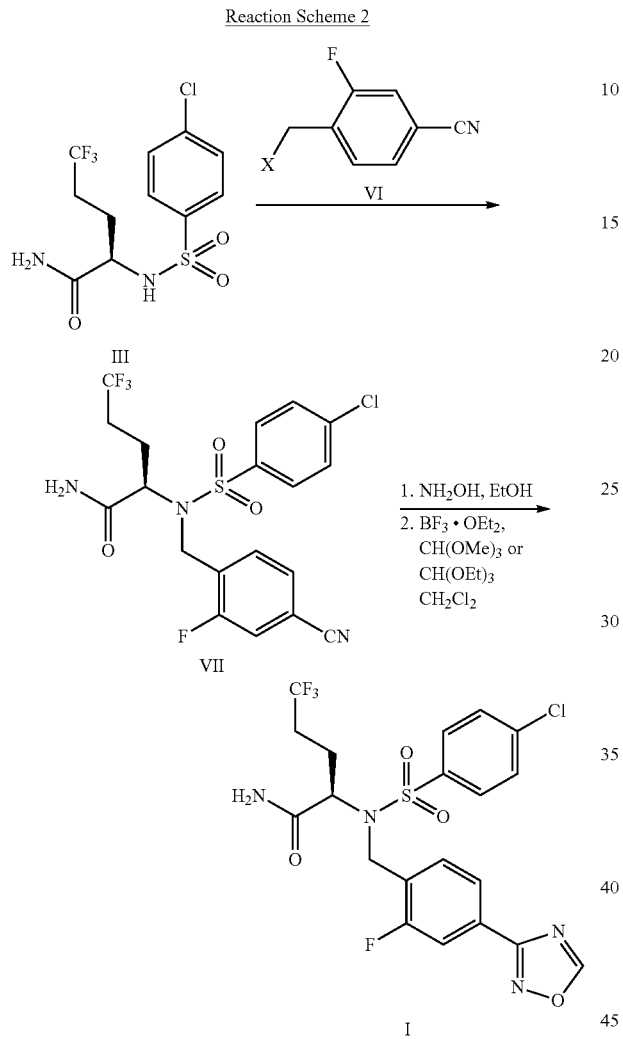

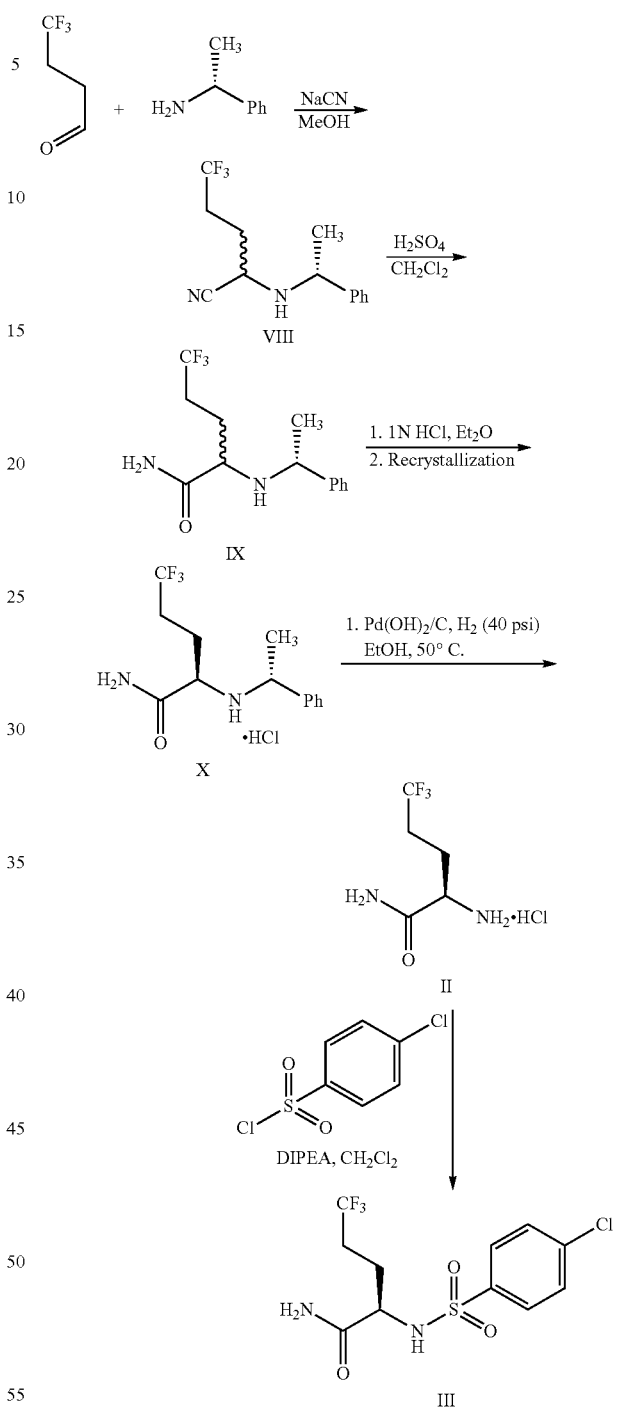

In another method of preparation illustrated in Reaction Scheme 2, the 1,2,4-oxadiazole compound of Formula I is prepared by alkylating the compound of Formula III with 2-cyano-4-fluorobenzyl derivative of Formula VI wherein X is a leaving group in the presence of a base in a suitable solvent to produce the nitrile of Formula VII. The desired compound of Formula I is then prepared from the nitrile compound of Formula VII using methods well-known to those skilled in the art (ref: Joule, J. A., et al., *Heterocyclic Chemistry*, 3rd ed., Chapman & Hall, London (1995) 452-456 and references cited therein). For example, reaction of the nitrile of Formula VII with hydroxylamine in an alcohol solvent such as methanol or ethanol at temperatures up to reflux provides an intermediate amide oxime that is subsequently treated with an orthoformate (such as triethyl or trimethyl orthoformate) in the presence of an acid source such as trifluoroacetic acid or boron trifluoride etherate in an inert organic solvent such as $CH_2Cl_2$, acetonitrile, tetrahydrofuran and the like to provide the 1,2,4-oxadiazole of Formula I.

Reaction Scheme 3 describes the preparation of (α-amino) acetamide of Formula II starting with commercially available trifluorobutyraldehyde and (R)-α-methyl benzyl amine under Strecker conditions with acetic acid and cyanide source such as sodium cyanide, potassium cyanide, or trimethylsilylcyanide in a suitable solvent such as methanol to afford the aminonitrile of Formula VIII as a mixture of diastereomers. The starting trifluorobutyraldehyde may also be prepared by oxidation of trifluorobutanol. Hydrolysis of the nitrile of Formula VIII to the corresponding amide of Formula IX is carried out with sulfuric acid and neutralization of the reaction, followed by acidification and recrystallization from a suitable solvent such as methanol, isopropanol, ethyl acetate, methyl tert-butyl ether, or mixtures thereof, to afford the amide of Formula X in >99% diastereomeric excess. The benzyl group may then be removed by hydrogenation in the presence of a suitable catalyst such as palladium hydroxide or palladium on carbon to give the amino amide of Formula II which may be sulfonylated with p-chlorosulphonyl chloride to afford the sulfonamide of Formula III.

Reaction Scheme 4

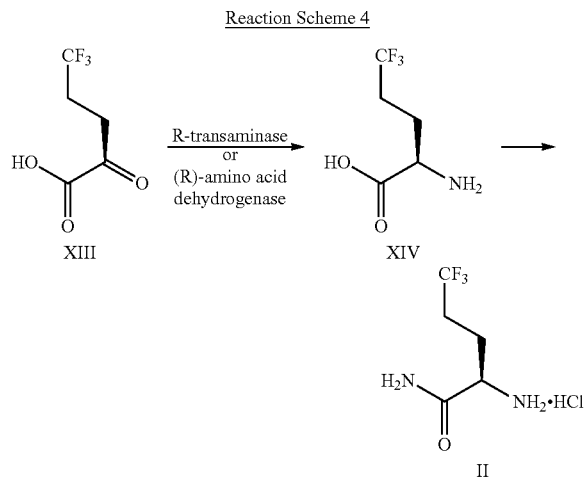

In another method of preparation, the (α-amino)acetamide of Formula II can be stereoselectivity produced using an enzymatic process starting with 5,5,5-trifluoro-2-oxopentanoic acid as illustrated in Reaction Scheme 4. The (R)-5,5,5-trifluoronorvaline of Formula XIV may be prepared in substantially enantiomerically pure form from the compound of Formula. XIII using commercially available (R)-aminotransferase enzyme by methods well known to those skilled in the art. In an alternate method, the enzymatic process may be carried out using the commercially available (R)-amino acid dehydrogenase enzyme. The enzymatic processes are carried out using the methods described below and methods well-known to those skilled in the art. The conversion of the (R)-5,5,5-trifluoronorvaline of Formula XIV to the compound of Formula II may be carried out using general procedures for amide preparation well-known in the art.

Reaction Scheme 5

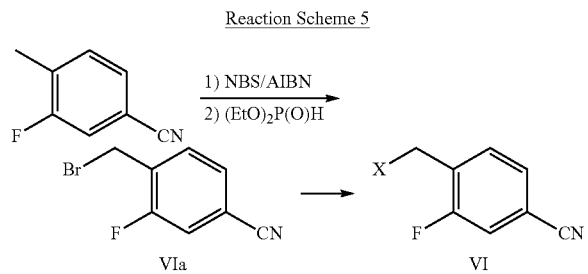

Benzyl bromide of Formula VIa may be prepared by bromination of commercially available 2-fluoro-4-cyanotoluene with N-bromosuccinimide in a suitable solvent such as dichloromethane, dichloroethane or carbon tetrachloride, using an initiator such as AIBN as illustrated in Reaction Scheme 5. The bromination proceeds in high yield and, if desired, the compound of Formula VIa may readily be converted to the compound of Formula VI wherein X is a leaving group by methods well-known to those skilled in the art, Reaction Scheme 6

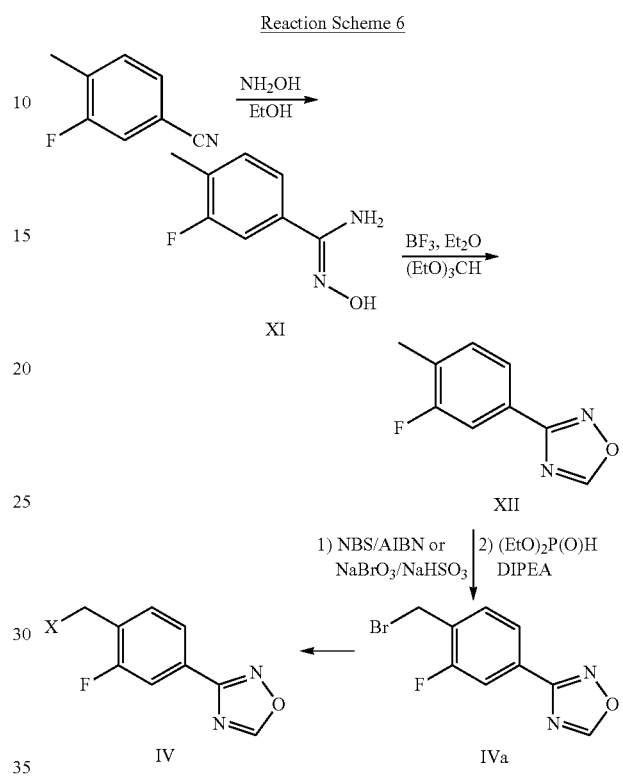

As an alternative to the use of the compound of Formula VI in the linear sequence to the sulfonamide oxadiazole of Formula I described above in Reaction Scheme 2, the preparation of the compound of Formula IV for use in the convergent route depicted in Reaction Scheme 1 is shown in Reaction Scheme 6. Treatment of commercially available 2-fluoro-4-cyanotoluene with hydroxylamine at room temperature in an alcohol solvent affords crude amide oxime of Formula XI, which may be directly employed in the subsequent reaction, Cyclization of the amide oxime of Formula XI by treatment with boron trifluoride etherate and triethyl orthoformate affords the oxadiazole of Formula XII in over 90% yield in two steps. As an alternative to the use of boron trifluoride, the cyclization can also be cleanly accomplished by employing trifluoroacetic acid as the acid source. Bromination with N-bromosuccinimide in a suitable solvent such as dichloromethane, dichloroethane, or carbon tetrachloride using an initiator such as AIBN affords the mono-bromo oxadiazole compound of Formula IVa. If it is desired to avoid possible mixtures of mono- and di-bromides, the toluoyl function of compound of Formula XI may deliberately be overbrominated with N-bromosuccinimide and AIBN to afford the corresponding dibromide which may then be reduced with diethyl phosphite to afford the mono-bromide of Formula VIa in over 90% yield. The dibromination and reduction may be accomplished in one pot without isolation of the dibromide in an overall yield of over 90%. Alternatively, the compound of Formula IVa may also be prepared from the compound of Formula XII with excess sodium bromate and sodium bisulfite in a suitable two-phase solvent system such as ethyl acetate/water, dichloromethane/water, butyl acetate/water, trifluorotoluene/water and the like to provide a mixture of mono- and di-bromide intermediates which is reduced in situ with diethyl phosphate/diisopropylamine to afford the monobromide of Formula IVa. If desired, the compound of Formula IVa may readily be converted to the compound of Formula IV wherein X is a leaving group by methods well-known to those skilled in the art.

In another embodiment, this invention includes pharmaceutical compositions comprising the compound of Formula I in combination with a pharmaceutical adjuvant, carrier or diluent.

In still another embodiment, this invention relates to a method of treatment of disorders responsive to the inhibition of β-amyloid peptide in a mammal in need thereof, which comprises administering to said mammal a therapeutically effective amount of the compound of Formula I or a solvate or hydrate thereof.

In yet another embodiment, this invention relates to a method for treating, alleviating or delaying the onset of Alzheimer's disease, cerebral amyloid angiopathy, systemic amyloidosis, hereditary cerebral hemorrhage with amyloidosis of the Dutch type, multi-infarct dementia, mild cognitive impairment and Down syndrome in a patient in need thereof, which comprises administering to said patient a therapeutically effective amount of the compound of Formula I or solvate or hydrate thereof.

For therapeutic use, the pharmacologically active compound of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous), transdermal, sublingual, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. Oral preparations include push-fit capsules made of gelatin, as well as soft, scaled capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. For topical or nasal administration, penetrants or permeation agents that are appropriate to the particular barrier to be permeated are used in the formulation. Such penetrants are generally known in the art. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences*, Mack Publishing Company, Easton, Pa., 17th edition, 1985.

The dosage of the compound of Formula I to achieve a therapeutic effect will depend not only on such factors as the age, weight and sex of the patient and mode of administration, but also on the degree of Aβ inhibition desired and the potency of the compound of Formula I for the particular disorder or disease concerned. It is also contemplated that the treatment and dosage of the compound of Formula I may be administered in unit dosage foam and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of the compound of Formula I or pharmaceutical composition thereof for a mammal, including man, suffering from, or likely to suffer from any condition related to Aβ peptide production as described herein, generally the daily dose will be from about 0.01 mg/kg to about 10 mg/kg and preferably, about 0.1 to 2 mg/kg when administered parenterally. For oral administration, the dose may be in the range from about 0.01 to about 20 mg/kg and preferably from 0.1 to 10 mg/kg body weight. The active ingredient will preferably be administered in equal doses from one to four times a day. However, usually a small dosage is administered, and the dosage is gradually increased until the optimal dosage for the host under treatment is determined. In accordance with good clinical practice, it is preferred to administer the instant compound at a concentration level that will produce an effective anti-amyloid effect without causing any harmful or untoward side effects. However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

Biological Data

PXR Transactivation

Pregnane X receptor (PXR) is a nuclear hormone receptor principally responsible for the induction of cytochrome P450 (CYP) 3A4, which plays a major role in metabolizing many clinically prescribed drugs. It is well known that the induction of CYP3A4 can cause either drug-drug interaction by increasing the metabolic clearance of co-administered CYP3A4 substrates (Bertilsson, G. et al., *Proc. Nat. Acad. Sci. USA* (1998) 95: 12208-12213; Lehmann, J. M. et al., *J. Clin. Invest.* (1998) 102: 1016-1023) or can cause loss of drug exposure due to autoinduction. Characterizing the induction potential of discovery or development drug candidates has become an important screen throughout the pharmaceutical industry. A PXR transactivation assay is used to assess the induction potential of CYP3A4, and a cytotoxicity assay of HepG2 cells is used to monitor the assay interference due to cytotoxicity.

Cell culture medium used is DMEM. Lipofectamine 2000, PBS, trypsin-EDTA (0.25%), and penicillin-streptomycin were purchased from GIBCO/Invitrogen (Carlsbad, Calif.). Heat-inactivated fetal bovine serum (FBS) was purchased from Sigma (St. Louis, Mo.). Charcoal/dextran treated fetal bovine serum (FBS) was purchased from Hyclone (Logan, Utah). HepG2 cells were obtained from ATCC (Manassas, Va.). Human PXR-pcDNA3 and luciferase reporter containing CYP3A4 promoter, CYP3A-Luc, were generated at Bristol-Myers Squibb. Black standard 384-well plates were purchased from BD Biosciences (Lexington, Ky.). Luciferase substrate (Steady-Glo) was purchased from Promega (Madison, Wis.). Control compound rifampicin was purchased from Sigma (St. Louis, Mo.).

Culture of HepG2 cells is performed in T175 flasks using DMEM containing 10% FBS. The transfection mixture contains 1 μg/mL of PXR-pcDNA3 plasmid DNA, 20 μg/mL of Cyp3A-Luc plasmid DNA, 90 μL/mL of Lipofectamine 2000, and serum-free medium. After incubating at room temperature for 20 minutes, the transfection mixture (1 mL per flask) is applied to the cells in fresh medium (20 mL per flask), and flasks incubated at 37° C. (5% $CO_2$) overnight.

Cells in each flask are washed with PBS and 4 mL of Trypsin-EDTA (0.25%) is added and incubated for one minute at room temperature. Trypsin is then aspirated off and flasks incubated for an additional five minutes at room temperature. The flasks are then tapped vigorously to break up cell aggregates. After the addition of 10 mL of DMEM containing 5% charcoal/dextran-treated FBS, the entire mixture is transferred to conical tubes. The pool of cells in suspension is further disaggregated by pipetting through a 1 mL pipet tip. Cells are then counted and diluted in media to $3.0 \times 10^5$ cells/mL. Fifty μL of cell mixture is added to each well of a black standard 384-well plate containing 0.25 μL of test compound dissolved in 100% DMSO. The plates are incubated at 37° C. (5% $CO_2$) overnight before 25 μL of luciferase substrate (Steady-Glo, Promega) is added to each well. After fifteen minutes, plates are read on a Viewlux (Perkin-Elmer) plate reader.

Rifampicin (10 μM), a well known agonist of PXR, is included in each plate as an internal standard and positive control. The data was then expressed as percent activation (% Act), where the total signal is the signal from the 10 μM rifampicin and the blank signal is that from the DMSO vehicle.

$$\% \text{ Act} = \frac{\text{Compound signal} - \text{Blank signal}}{\text{Total signal} - \text{Blank signal}} \times 100\%$$

Compounds are tested at ten concentrations (50 μM-2.5 nM, 1:3 serial dilution), and XL-Fit (IDBS, Inc.) used for curve-fitting. Concentrations of compound at which 20% and 60% activation occur (EC20A and EC60A, respectively) are reported.

The human pregnane-X receptor is principally responsible for the induction of CYP3A4, as well as CYP2B6, CYP2C8/9, Phase 2 enzymes such as UGT, and several transporters such as P-gp, MRP2, and OATP2. The above test demonstrated that (2R)-2-[[(4-chlorophenyl)sulfonyl][[2-fluoro-4-(1,2,4-oxadiazol-3-yl)phenyl]methyl]amino]-5,5,5-trifluoropentanamide had an $EC_{20A}$ (20% of the Rifampicin response at 10 μM) of 6.9 μM and an $EC_{60A}$ (60% of the Rifampicin response at 10 μM) of greater than 16.7 μM in the hPXR transactivation assay. These results suggest that (2R)-2-[[(4-chlorophenyl)sulfonyl][[2-fluoro-4-(1,2,4-oxadiazol-3-yl)phenyl]methyl]amino]-5,5,5-trifluoropentanamide may have the potential to be an inducer of human CYP3A4 through the activation of hPXR.

Induction of Cytochrome P450 in Fa2N-4 Cells

The ability of (2R)-2-[[(4-chlorophenyl)sulfonyl][[2-fluoro-4-(1,2,4-oxadiazol-3-yl)phenyl]methyl]amino]-5,5,5-trifluoropentanamide to induce CYP3A4 mRNA was evaluated in vitro using the Fa2N-4 cell line. The Fa2N-4 cell is an immortalized human hepatocyte line that was created using the Simian virus 40 (SV40) T antigen as the immortalizing gene, while retaining basal expression and inducibility of several CYP isoforms, including CYP3A4. Fa2N-4 cells and MFE Support Media F were provided by XenoTech, LLC (Lenexa, Kans.).

Fa2N-4 cells were supplied on 12-well, collagen-coated plates at a seeding density of $0.67 \times 10^6$ cells per well. Upon the receipt of the cells, the media were changed and the cells maintained overnight in a humidified, $CO_2$-supplied incubator. After this adaptation period, the cells were examined under a light microscope and a determination was made as to whether the cells were morphologically normal and suitable for use. During the treatment period, the cells were visually inspected on a daily basis; cellular morphology, confluency, and signs of toxicity due to the test article were documented as necessary. The cell cultures were treated with 4 concentrations (0.5, 2, 8, and 20 μM in final incubation) of (2R)-2-[[(4-chlorophenyl)sulfonyl][[2-fluoro-4-(1,2,4-oxadiazol-3-yl)phenyl]methyl]amino]-5,5,5-trifluoropentanamide, and a solvent vehicle control (0.1% DMSO) in triplicate: Rifampicin (10 μM), a prototypical CYP3A4 inducer, was used as the positive control. Fa2N-4 cells were exposed to the test articles for a total of 3 days. The culture medium was replaced daily with fresh medium containing the test articles. After a total of ~72 hours of exposure, medium was aspirated and the cells washed once with warm phosphate buffered saline solution before adding the cell lysis buffer (Qiagen, Valencia, Calif.).

The ability of (2R)-2-[[(4-chlorophenyl)sulfonyl][[2-fluoro-4-(1,2,4-oxadiazol-3-yl)phenyl]methyl]amino]-5,5,5-trifluoropentanamide to induce CYP3A4 mRNA expression was examined in Fa2N-4 immortalized human hepatocytes. Treatment of Fa2N-4 hepatocytes with rifampicin (10 μM) for 3 days caused a significant (12-fold) increase in cellular CYP3A4 mRNA expression, indicating that the cells were properly functioning. Incubation of hepatocytes with (2R)-2-[[(4-chlorophenyl)sulfonyl][[2-fluoro-4-(1,2,4-oxadiazol-3-yl)phenyl]methyl]amino]-5,5,5-trifluoropentanamide for 3 days resulted in a concentration-dependent increase in CYP3A4 mRNA expression, reaching 2.6-fold over the vehicle control at the highest concentration tested (20 μM). This magnitude of induction was equivalent to 22% of the induction response caused by rifampicin, suggesting that (2R)-2-[[(4-chlorophenyl)sulfonyl][[2-fluoro-4-(1,2,4-oxadiazol-3-yl)phenyl]methyl]amino]-5,5,5-trifluoropentanamide could moderately induce CYP3A4 at concentrations greater than 20 μM. Relatively minimal induction of CYP3A4 (≦2.0-fold) was observed at lower concentrations of (2R)-2-[[(4-chlorophenyl)sulfonyl][[2-fluoro-4-(1,2,4-oxadiazol-3-yl)phenyl]methyl]amino]-5,5,5-trifluoropentanamide (≦8.0 μM).

Metabolic Stability in Liver Microsomes

Mouse, rat, dog, human, and cynomolgus monkey liver microsomes were obtained from BD Gentest (Woburn, Mass.). The lot numbers were 13 (mouse), 8 (rat), 8 (dog), 19 and 26 (human), and 3 (cynomolgus monkey). The oxidative metabolism of (2R)-2-[[(4-chlorophenyl)sulfonyl][[2-fluoro-4-(1,2,4-oxadiazol-3-yl)phenyl]methyl]amino]-5,5,5-trifluoropentanamide was studied in liver microsomes under three sets of conditions. The incubation mixtures for human and dog (total volume 3 mL, organic solvent content 0.3%) contained (2R)-2-[[(4-chlorophenyl)sulfonyl][[2-fluoro-4-(1,2,4-oxadiazol-3-yl)phenyl]methyl]amino]-5,5,5-trifluoropentanamide (1 µM), microsomal protein (1 mg/mL), NADPH (1 mM), Tris chloride buffer (100 mM, pH 7.4), and magnesium chloride (3.3 mM). The reaction, conducted in triplicate, was initiated by the addition of NADPH followed by incubation at 37° C. for 50 minutes. Aliquots of samples (0.25 mL) were taken at 0, 5, 10, 20, 30, 40 and 50 minutes and the reaction was quenched by the addition of 3 volumes of acetonitrile. The incubation mixtures for cynomolgus monkey and rat (total volume 3 mL, organic solvent content 0.3%) contained (2R)-2-[[(4-chlorophenyl)sulfonyl] [[2-fluoro oxadiazol-3-yl)phenyl]methyl]amino]-5,5,5-trifluoropentanamide (1 µM), microsomal protein (0.1 mg/mL), NADPH (1 mM), Tris chloride buffer (100 mM, pH 7.4), and magnesium chloride (3.3 mM). The reaction, conducted in triplicate, was initiated by the addition of NADPH followed by incubation at 37° C. for 50 minutes. Aliquots of samples (0.25 mL) were taken at 0, 5, 10, 20, 30, 40 and 50 minutes and the reaction was quenched by the addition of 3 volumes of acetonitrile. The incubation mixtures for mouse and cynomolgus monkey (total volume 3 mL, organic solvent content 0.3%) contained (2R)-2-[[(4-chlorophenyl)sulfonyl][[2-fluoro-4-(1,2,4-oxadiazol-3-yl)phenyl]methyl]amino]-5,5,5-trifluoropentanamide (1 µM), microsomal protein (0.1 mg/mL), NADPH (1 mM), Tris chloride buffer (100 mM, pH 7.4), and magnesium chloride (3.3 mM). The reaction, conducted in duplicate, was initiated by the addition of NADPH followed by incubation at 37° C. for 40 minutes. Aliquots of samples (0.25 mL) were taken at 0, 5, 10, 15, 20, 30 and 40 minutes and the reaction was quenched by the addition of 3 volumes of acetonitrile. For all studies, samples were analyzed immediately by an LC/MS method. Rate of parent disappearance was calculated from the peak area ratios of (2R)-2-[[(4-chlorophenyl)sulfonyl][[2-fluoro-4-(1,2,4-oxadiazol-3-yl)phenyl]methyl]amino]-5,5,5-trifluoropentanamide at each time point.

The hepatic intrinsic clearance (CLh, int, mL/min/kg) of (2R)-2-[[(4-chlorophenyl)sulfonyl][[2-fluoro-4-(1,2,4-oxadiazol-3-yl)phenyl]methyl]amino]-5,5,5-trifluoropentanamide in various species was estimated from liver microsome data using the method described by Houston J B., *Biochem Pharmacol* 1994; 47:1469-1479; Iwatsubo, et al., *Pharmacol Ther* (1997) 73:147-171; and Obach et al., *J Pharmacol Exp Ther* (1997) 283:46-58.

The rate of in vitro metabolism was determined for (2R)-2-[[(4-chlorophenyl)sulfonyl][[2-fluoro-4-(1,2,4-oxadiazol-3-yl)phenyl]methyl]amino]-5,5,5-trifluoropentanamide in the presence of NADPH-fortified liver microsomes of various species. The compound of the present invention (2R)-2-[[(4-chlorophenyl)sulfonyl][[2-fluoro-4-(1,2,4-oxadiazol-3-yl)phenyl]methyl]amino]-5,5,5-trifluoropentanamide (1 µM) was metabolized at a rate of 690, 630, 40, 495 and 32 pmol/min/mg protein in the presence of mouse, rat, dog, cynomolgus monkey, and human microsomes, respectively. When the rates of (2R)-2-[[(4-chlorophenyl)sulfonyl][[2-fluoro-4-(1,2,4-oxadiazol-3-yl)phenyl]methyl]amino]-5,5,5-trifluoropentanamide consumption were scaled to in vivo clearance, the predicted in vivo (serum) clearance values of (2R)-2-[[(4-chlorophenyl)sulfonyl][[2-fluoro-4-(1,2,4-oxadiazol-3-yl)phenyl]methyl]amino]-5,5,5-trifluoropentanamide were approximately 87, 52, 14, 39 and 8 mL/min/kg in mouse, rat, dog, cynomolgus monkey, and human, respectively. These data suggest that (2R)-2-[[(4-chlorophenyl)sulfonyl][[2-fluoro-4-(1,2,4-oxadiazol-3-yl)phenyl]methyl]amino]-5,5,5-trifluoropentanamide is anticipated to be a low clearance compound in human.

In Vitro Pharmacology

Presenilin Binding Assay

Radioligand displacement assays with [$^3$H] (R)-4-((N-(1-amino-4-methyl-1-oxopentan-2-yl)-4-chlorophenylsulfonamido)methyl)-N-(2-methoxyethyl)benzamide were carried out using a method previously described for [$^3$H] (2R,3S)-2-isobutyl-N1-((S)-2-oxo-1-(3-phenoxybenzyl)azepan-3-yl)-3-propylsuccinimide (RE987, compound A [Seiffert D, et al. Presenilin-1 and -2 are molecular targets for γ-secretase inhibitors. *J. Biol. Chem.* (2000) 275(44): 34086-34091]). Several experiments were performed to confirm that [$^3$H] (R)-4-((N-(1-amino-4-methyl-1-oxopentan-2-yl)-4-chlorophenylsulfonamido)methyl)-N-(2-methoxyethyl)benzamide bound to γ-secretase. First, the specific binding of [$^3$H] (R)-4-((N-(1-amino-4-methyl-1-oxopentan-2-yl)-4-chlorophenylsulfonamido)methyl)-N-(2-methoxyethyl)benzamide to membranes from wild-type and PS-1/PS-2 knockout fibroblasts showed that [$^3$H] (R)-4-((N-(1-amino-4-methyl-1-oxopentan-2-yl)-4-chlorophenylsulfonamido)methyl)-N-(2-methoxyethyl)benzamide bound specifically to membranes from wild-type fibroblasts but not knockout fibroblasts and that the specific signal was competed by structurally distinct γ-secretase inhibitors. Second, the pharmacology of [$^3$H] (R)-4-((N-(1-amino-4-methyl-1-oxopentan-2-yl)-4-chlorophenylsulfonamido)methyl)-N-(2-methoxyethyl)benzamide binding was investigated with several γ-secretase inhibitors. These results showed that displacement of [$^3$H] (R)-4-((N-(1-amino-4-methyl-1-oxopentan-2-yl)-4-chlorophenylsulfonamido)methyl)-N-(2-methoxyethyl)benzamide binding to THP-1 membranes correlated well with γ-secretase potency both as measured using previous radioligand binding assays and inhibition of Aβ formation in cultured cells.

THP-1 cells were grown in Spinner cultures in RPMI 1640 containing L-glutamine (Life Technologies Inc.) and 10 µM β-mercaptoethanol to a cell density of $5 \times 10^5$/mL. Cells were harvested by centrifugation, and pellets, containing $2 \times 10^8$ cells, were quick frozen in dry ice/ethanol and stored at −70° C. prior to use. On the day of the assay, cells were thawed at $2 \times 10^8$ cells per 10 mL of homogenization buffer consisting of 50 mM HEPES pH 7.0 containing a protease inhibitor cocktail of 104 µM 4-(2-aminoethyl)benzenesulfonyl fluoride hydrochloride, 80 nM aprotinin, 2 µM leupeptin, 4 µM bestatin, 1.5 µM pepstatin A, and 1.4 µM E-64 (0.1% of protease inhibitor cocktail P8340, Sigma-Aldrich, St. Louis, Mo.) at 4° C. The cells were homogenized using a Polytron (Brinkman, Westbury, N.Y.) at 18,000 rpm for 15 seconds, then centrifuged at 18,000 rpm, 4° C., 15 minutes in a Sorval RCSB centrifuge. The resulting pellet was resuspended in buffer at 4° C. to yield a total protein concentration of 5 mg/mL. For use in the binding assay, the cell homogenate was diluted to a concentration of 300 µg/mL in assay buffer consisting of 50 mM HEPES pH 7.0, 0.1% CHAPSO. Assays were initiated in polypropylene 96-well plates (Costar, Cambridge, Mass.) by the addition of 200 µL of cell homogenate to 50 µL of assay buffer containing 0.75 nM radioligand ([$^3$H] (R)-4-((N-(1-amino-4-methyl-1-oxopentan-2-yl)-4-chlorophenylsulfonamido)methyl)-N-(2-methoxyethyl)benzamide, 110 Ci/mmol) and various concentrations of unlabelled compounds, and incubated for 1 hour at 37° C. Final DMSO concentration was 1%. Separation of bound from free radioligand was by filtration on GFF glass fiber filters (Innotech Biosystems International, Lansing, Mich.) using an Innotech cell harvester. Filters were washed three times with 0.3 mL per well of phosphate buffered saline pH 7.0 at 4° C. and radioactivity was measured using a Wallac 1450 Microbeta liquid scintillation counter (PerkinElmer, Boston, Mass.). Ki values of competing compounds were derived through Cheng-Prussoff correction of $IC_{50}$ values calculated using XLfit (IDBS, Guildford, UK).

The above radioligand binding assay was used to measure affinity of compounds to the presenilin target site of the γ-secretase complex. (2R)-2-[[(4-Chlorophenyl)sulfonyl] [[2-fluoro-4-(1,2,4-oxadiazol-3-yl)phenyl]methyl]amino]-5, 5,5-trifluoropentanamide caused a dose-dependent inhibition of [$^3$H] (R)-4-((N-(1-amino-4-methyl-1-oxopentan-2-yl)-4-chlorophenylsulfonamido)methyl)-N-(2-methoxyethyl)benzamide binding to presenilin in THP-1 membranes. Analysis of multiple experiments yielded Ki=0.48 nM±0.24 nM (mean±SD, n=8).

Inhibition of Aβ Formation in Cultured Cells

Compounds were assayed for Aβ40 or Aβ42 inhibition in cells using H4 APP751 SWE clone 8.20, developed at Bristol-Myers Squibb, an H4 neuroglioma cell line stably expressing the Swedish mutant of APP751. Cells were maintained in log phase through twice weekly passage at a 1:20 dilution. For $IC_{50}$ determinations, 30 μL cells (1.5×10$^4$ cells/well) in DMEM media containing 0.0125% BSA (Sigma A8412) were plated directly into 384-well compound plates (Costar 3709) containing 0.1 μL serially diluted compound in DMSO. Following incubation for 19 hours in 5% $CO_2$ at 37° C., plates were briefly centrifuged (1000 rpm, 5 min). A 10 μL aliquot from each well was transferred to a second assay plate (Costar 3709) for Aβ40 measurements. Antibody cocktails were freshly prepared by dilution into 40 mM Tris-HCl (pH 7.4) with 0.2% BSA and added to assay plates. For Aβ42 measurements, antibodies specific for the Aβ42 neoepitope (565, developed at Bristol-Myers Squibb; conjugated to the Wallac reagent (Perkin Elmer)) and the N-terminal sequence of Aβ peptide (26D6, developed at SIBIA/Bristol-Myers Squibb; conjugated to APC (Perkin Elmer)) were mixed and 20 μL of the mixture was added to each well of the incubated cell plate yielding a final concentration of 0.8 ng/well 565 and 75 ng/well 26D6. For the Aβ40 measurements, antibodies specific for the Aβ40 neoepitope (TSD, developed at Bristol-Myers Squibb; conjugated to the Wallac reagent (Perkin Elmer)) and 26D6 as described above were mixed and 20 μL of the mixture was added to the 10 μL aliquots which had been removed previously from the cell plate yielding a final concentration of 1.6 ng/well TSD and 17.5 ng/well 26D6. Assay plates containing antibodies were sealed with aluminum foil and incubated overnight at 4° C. Signal was determined using a Viewlux counter (Perkin Elmer) and $IC_{50}$ values determined using curve fitting in CurveMaster (Excel Fit based).

(2R)-2-[[(4-Chlorophenyl)sulfonyl][[2-fluoro-4-(1,2,4-oxadiazol-3-yl)phenyl]methyl]amino]-5,5,5-trifluoropentanamide potently inhibited the formation of Aβ40 and Aβ42 in H4-8Sw cells, Analysis of multiple experiments yielded $IC_{50}$=0.30±0.15 nM (mean±SD, n=50) for Aβ40 inhibition and $IC_{50}$=0.27±0.12 nM (mean±SD, n=45) for Aβ42 inhibition.

Inhibition of Notch Signaling in Cultured Cells

γ-Secretase activity is required for signaling by the Notch family of transmembrane receptors. Since inhibition of Notch signaling causes undesired, mechanism-based side effects, a cellular assay for Notch1-ΔE signaling was used to counterscreen γ-secretase inhibitors.

A mouse Notch1 expression construct was generated by PCR using standard molecular biology techniques and verified by sequencing. This construct was generated in the pCDNA3.1+ Hyg vector (Invitrogen) modified to contain a N-terminal 20 amino acid signal sequence and a C-terminal 7X myc tag. The signal sequence was derived from mouse Notch1; the 7X myc-tag was created by using overlapping primers and subcloned into the HindIII/XhoI sites of the pCDNA3.1+Hyg vector.

The mouse Notch1-ΔE construct contains the mouse Notch1 signal sequence and the M1727V mutation within the transmembrane domain to suppress internal translation initiation. Mouse Notch1-ΔE coding sequence from amino acid 1704 to 2193 was isolated from a Mouse Spleen Quick Clone cDNA library (Clontech) and subcloned into the modified vector containing the 7X myc-tag and the signal sequence as a XbaI/HindIII fragment.

Hela cells were maintained in DMEM (GibcoBRL) containing 10% FBS (GibcoBRL), Penicillin/Streptomycin (GibcoBRL) and 2 mM L-glutamine (GibcoBRL). Cells were transiently transfected using TransIT-HelaMONSTER (Mires) according to the manufacturer's directions. Hela cells (ATCC) were plated 16 hours before transfection at a density of 4×10$^6$ cells per T175 flask in Hela growth media (DMEM (high glucose with HEPES) with glutamine, penicillin, streptomycin and 10% fetal bovine serum). Cells were transfected in growth media with: 6 μg mouse Notch1-ΔE plasmid, 15.6 μg carrier plasmid (pCDNA3.1+ hyg), 14.4 μg CBF1 plasmid (luciferase reporter) using HelaMonster Transfection Reagent (Mirus). The CBF1-luciferase reporter construct consists of 4X copies of the CBF1 binding element upstream of the SV40 promoter (pGL3-Promoter, Promega). The CBF1-luciferase reporter was generated using overlapping primers to generate the 4X CBF1 binding region. This fragment was subcloned into the NheI/BglII sites of pGL3-Promoter constructs. The integrity of this construct was confirmed by sequencing. DNA stocks were diluted in TE buffer (10 mM Tris, 1 mM EDTA, pH 8.0) for transfection. Five to six hours after DNA addition, cells were removed from the flask with Trypsin-EDTA and resuspended in defined media (DMEM (high glucose with HEPES) with glutamine, penicillin, streptomycin, 0.0125% bovine serum albumin and non-essential amino acids) at a concentration of 5×10$^4$ cells/mL. Cells were plated into 96 well black Clearview plates (Packard) at a volume of 200 μL/well (1×10$^4$ cells) and incubated at 37° C. for 1.5 hours to allow cells to adhere to the plates. Test compounds were initially diluted in a 96 well polypropylene plate in 100% DMSO. The DMSO compound stocks were then diluted 47.6-fold by transferring into a plate containing defined media yielding a 2.1% DMSO concentration. Diluted compound solutions (10 μL) were added to the cell plate yielding a final 0.1% DMSO concentration. Cell plates containing compound were incubated overnight at 37° C. Following this overnight incubation, media was gently removed and 25 μL of phosphate buffered saline (with calcium and magnesium) was added to each well. Luc-Screen (Applied Biosystems) reagents A and B were mixed in equal proportions and 50 μL of the mixture was added to each well. The plate was incubated at room temperature for 10 minutes before black backing was attached to the bottom of the plate and the signal was read on a TopCount (Packard). Concentration response curves were then fit using nonlinear regression to determine $IC_{50}$ values.

γ-Secretase activity is required for signaling by the Notch family of transmembrane receptors. Since inhibition of Notch signaling causes undesired, mechanism-based side effects, the cellular assay for Notch1-ΔE signaling described above was used to counterscreen γ-secretase inhibitors. Analysis of multiple experiments for inhibition of Notch1-ΔE signaling by (2R)-2-[[(4-chlorophenyl)sulfonyl][[2-fluoro-4-(1,2,4- oxadiazol-3-yl)phenyl]methyl]amino]-5,5,5-trifluoropentanamide yielded $IC_{50}=58\pm23$ nM (mean±SD, n=58).

Based on the cellular potencies for inhibiting Aβ40 (0.3 nM) and Notch (58 nM), the Notch/APP selectivity for (2R)-2-[[(4-chlorophenyl)sulfonyl][[2-fluoro-4-(1,2,4-oxadiazol-3-yl)phenyl]methyl]amino]-5,5,5-trifluoropentanamide is 193X (95% CI=163-232).

In Vivo Pharmacology

Abeta ELISAs

Aβ species from animals were measured using sandwich ELISA assays. A brief discussion of these assays is included here since the details of the epitopes for the individual antibodies determines the Aβ species that are detected. Mouse and rat Aβ share a common Aβ sequence that differs from human Aβ. As a result of these sequence differences, antibodies that recognize the N-terminal region of human Aβ, such as 26D6, bind weakly to rodent Aβ. Likewise, antibodies that bind tightly to rodent Aβ, such as 252, bind weakly to human Aβ. Two assays were developed for measuring rodent Aβ40: 252-TSD and 4G8-TSD. The TSD-4G8 assay can measure not only Aβ40, but other BACE-γ-secretase cleavage products (Aβ11-40) and α-secretase-γ-secretase cleavage products (P3). Table 1 summarizes the assays presented in this application and their use.

TABLE 1

Summary of Antibody Pairs Used to Assay In Vivo Samples

| Antibody Pair | Tissues analyzed | Aβ species detected |
|---|---|---|
| 252-TSD | Rat brain | Aβx-40[a] |
| 4G8-TSD | Rat plasma, CSF | Aβx-40 & P3 |

[a]The exact location of "x" is unknown. While 252 recognizes the N-terminal region of Aβ, it is unknown whether amino terminal truncation of Aβ affects 252 binding. This uncertainty is unlikely to be an issue in rats since N-terminal truncation is rare.

Each of these assays was validated using several methods. First, varying amounts of synthetic Aβ were added to the biological matrix and the increase in signal was compared to that obtained with synthetic Aβ in buffer solution. Second, Aβ was depleted from the biological sample with anti-Aβ antibodies. Third, samples were assayed from animals that were treated with high doses of a γ-secretase inhibitor. A validated assay efficiently detected exogenously added Aβ (>80% recovery), had a greatly reduced signal after Aβ immunodepletion (>80% reduction compared to nonspecific controls), and had a signal reduced to values approaching or overlapping with the assay floor using samples from animals treated with high doses of a γ-secretase inhibitor. The optimized and validated Aβ assays still contained a small amount of the signal (5-20% of vehicle control) which could not be depleted by anti-Aβ antibodies or treatment with γ-secretase inhibitors. This signal is unlikely to be Aβ and is consequently referred to as the assay floor. The assay floor was not used to correct any of the Aβ measurements and consequently, the values reported are likely underestimates of the actual amount of Aβ inhibition.

Aβ40 was used as a surrogate for Aβ42 in vivo. Aβ40 is approximately 10-fold more abundant in biological samples than Aβ42. Aβ40 is a good surrogate for Aβ42 based on experiments in cultured cells where Aβ40 and Aβ42 were similarly inhibited by (2R)-2-[[(4-chlorophenyl)sulfonyl][[2-fluoro-4-(1,2,4-oxadiazol-3-yl)phenyl]methyl]amino]-5,5,5-trifluoropentanamide and other γ-secretase inhibitors.

Rat Studies

In Life

Female Harlan Sprague-Dawley rats (~200-250 g) were dosed daily by oral gavage with a dosing vehicle of 99% PEG-400, 1% Tween-80 at 4 mL/kg in the morning. Dosing solutions were made once at the start of the study. Heating at 56° C. and sonication were used to solubilize compound in the dosing solution. All procedures were done in concordance with ACUC guidelines. Terminal blood samples were obtained by cardiac puncture after $CO_2$ euthanasia and collected in EDTA tubes. Plasma was obtained after centrifugation. Brain tissue was dissected, weighed and frozen on dry ice until analysis. CSF samples were centrifuged to remove cells or debris prior to dilution at 1:2 in 4% BSA and frozen for subsequent analysis. Histopathological samples were placed in neutral buffered formalin prior to processing. Samples collected for occupancy were coated in embedding matrix, and frozen at −25° C. to −30° C. in a 2-methylbutane bath followed by dry ice. In life plasma samples were obtained using retro-orbital bleeding.

Brain Abeta40 Assay

Rat brain (half a hemisphere) was homogenized using a polytron at 4 mL/g in PBS, pH 7.8, 2% CHAPS, complete protease inhibitors (Roche). Large debris was removed by centrifugation for 30 minutes at 20,800×g and the resulting supernatant was diluted 1:2 in PBS, 2.5% BSA. White Microlite II ELISA plates (Thermo Electron) were incubated with 50 μg/mL TSD9S3.2 antibody in PBS for 1 hour at 37° C. Plates were blocked with 200 μL 5% bovine serum albumin (BSA; weight/volume prepared in PBS) for 2 hours at room temperature on a plate shaker and then washed 5 times with 500 μL/well of PBS, 0.05% Tween-20. Clarified brain homogenates were loaded in 6 replicates of 50 μL per well and incubated for 1 hour at room temperature. Plates were washed as before and then incubated with horse radish peroxidase (HRP)-conjugated 252 antibody (Biosource) diluted 1:2000 in PBS, 0.05% Tween, 0.1% BSA for 1 hour. Three replicates contained the 252-HRP antibody only and three replicates contained the 252-HRP antibody with 1 μg/mL rat Aβ1-14 (Anaspec) which competed specifically bound antibody; this background signal was substrated from the total signal to yield the specific signal. The bound 252-HRP antibody was detected using Pierce Supersignal Pico Chemiluminescent substrate for 10 minutes and quantified a Packard TopCount. Samples were normalized to a brain homogenate reference placed on each plate. Based on Aβ40 standard curves, the LLQ was 10 pg/mL and the LLD was 20 pg/g tissue.

Plasma Abeta40 Assay

Plates were coated with TSD antibody and washed as for the brain Aβ40 assay. Plasma samples were diluted 1:3 in PBS buffer, pH 7.8, 0.25% nonidet P40, 2.5% BSA. Samples were loaded in 6 replicates of 50 μL per well and incubated for 1-2 hours at room temperature. Samples were detected using 4G8-biotin (Signet) diluted 1:8000 in PBS, 0.05% Tween, 0.1% BSA for 1 hour. Three replicates had the 4G8-biotin antibody only and three replicates had the 4G8-biotin antibody with 1 μg/mL Aβ17-24 which competed the specific signal and thereby established a background value for each sample. Following washing as above, plates were incubated with streptavidin-HRP (Zymed) diluted 1:50,000 in PBS, 0.05% Tween, 0.1% BSA for 10 minutes. Detection and quantification were as for brain Aβ40 assays. Samples were normalized to a plasma reference placed on each plate. Based on Aβ40 standard curves, the LLQ was 7.5 pg/mL and the LLD was 23 pg/mL plasma.

CSF Abeta40 Assay

Plates were coated with TSD antibody and washed as for the brain Aβ40 assay. CSF samples were diluted 1:10 in PBS, pH 7.8, 0.1% Tween-20. At time of collection, CSF was previously diluted 1:2 in 4% BSA in water. Samples were loaded in 3 replicates of 50 μL per well and incubated for 1-2 hours at room temperature. Samples were detected using 4G8-biotin (Signet) diluted 1:8000 in PBS, 0.05% Tween, 0.1% BSA for 1 hour. Because the background was low, it was not necessary to run replicate samples with a competing peptide for this assay. Bound 4G-8-HRP was detected and quantified as for the plasma Aβ40 assay. Samples were normalized to a CSF reference placed on each plate. Based on Aβ40 standard curves, the LLQ was 20 pg/mL and the LLD was 400 pg/mL CSF.

Gamma-Secretase Site Occupancy

Brain sections were cut coronally at a thickness of 20 μm on a cryostat and thaw-mounted onto Superfrost Plus slides. Sections were saved at the level of the rostral hippocampus, with 3 sections per slide at intervals of about 120 μm, and frozen at −20° C. until use. For occupancy studies, brain sections were warmed to room temperature, dried, incubated for 10 minutes in 50 mM HEPES buffer, pH 7.4, then transferred to the same buffer containing 1.5 nM [³H]IN973 (Goldstein, M. E. et al., *J. Pharmacol. Exp. Ther.* (2007) 323:102-108) or [³H] (R)-4-((N-(1-amino-4-methyl-1-oxopentan-2-yl)-4-chlorophenylsulfonamido)methyl)-N-(2-methoxyethyl)benzamide and incubated at room temperature for 10 minutes. To define nonspecific binding, adjacent sections were incubated in buffer containing [³H]IN973 or [³H] (R)-4-((N-(1-amino-4-methyl-1-oxopentan-2-yl)-4-chlorophenylsulfonamido)methyl)-N-(2-methoxyethyl)benzamide, but including unlabeled γ-secretase inhibitor at 0.5 μM. After the incubation, the slides were washed three times for 2 minutes each in ice-cold PBS, pH 7.2, dipped in ice-cold distilled water, and dried with a fan blowing cool air. The slides were placed under tritium-sensitive phosphor storage screens (Amersham Biosciences, Arlington Heights, Ill.) and exposed in the dark for 7 days. Images were acquired from the phosphor storage screens using a Cyclone phosphor scanner (Packard, Meriden, Conn.) and OptiQuant acquisition and analysis software (Packard). Optical densities (expressed as digital light units per square millimeter) over areas of interest were measured and expressed as a percent of vehicle control.

Histopathology Methods

Following euthanasia by $CO_2$ asphyxiation, approximately 3 cm long sections of the proximal duodenum were removed from the abdomen, rinsed with ice cold Phosphate buffered saline and placed into 10% buffered formalin prior to sectioning. Tissue sections of the duodenum were embedded in liquid paraffin, mounted onto blocks, and cut into triplicate sagittal (cross-luminal) ring sections and stained using the Periodic acid Schiff's base method prior to microscopic evaluation. All animals survived until scheduled necropsy was performed.

Acute Rat Studies

A single dose of (2R)-2-[[(4-chlorophenyl)sulfonyl][[2-fluoro-4-(1,2,4-oxadiazol-3-yl)phenyl]methyl]amino]-5,5,5-trifluoropentanamide at 30 mg/kg significantly reduced both plasma Aβ40 and brain Aβ40 to levels of 2% and 16% of vehicle control, respectively. To further investigate the effect of (2R)-2-[[(4-chlorophenyl)sulfonyl][[2-fluoro-4-(1,2,4-oxadiazol-3-yl)phenyl]methyl]amino]-5,5,5-trifluoropentanamide in rats, a single dose of (2R)-2-[[(4-chlorophenyl)sulfonyl][[2-fluoro-4-(1,2,4-oxadiazol-3-yl)phenyl]methyl]amino]-5,5,5-trifluoropentanamide was administered at 1 mg/kg, 10 mg/kg, and 100 mg/kg and tissues were collected after 2, 5, 8, 12, and 24 hours for plasma Aβ40, brain Aβ40, and γ-secretase site occupancy measurements. These measurements showed that 10 mg/kg and 100 mg/kg reduced plasma Aβ40 and brain Aβ40 to less than 25% of baseline Aβ40 values from 2 to 24 hours post dosing. In contrast, 1 mg/kg did not cause a statistically significant change in brain Aβ40, but instead caused a transient rise in plasma Aβ40. In particular, plasma Aβ40 increased to 250% of starting values by 8 hours before returning to baseline values by 24 hours. γ-Secretase site occupancy showed that greater than 94% of γ-secretase inhibitor binding sites in the brain were occupied throughout the dosing interval following the 100 mg/kg dose and in all but the 24 hr timepoint (88%) following the 10 mg/kg dose. In contrast, only 75% of the brain γ-secretase binding sites were occupied two hours after the 1 mg/kg dose and site occupancy gradually returned to baseline values by 24 hours.

Results from acute rat studies showed that (2R)-2-[[(4-chlorophenyl)sulfonyl][[2-fluoro-4-(1,2,4-oxadiazol-3-yl)phenyl]methyl]amino]-5,5,5-trifluoropentanamide reduced plasma Aβ40, brain Aβ40, and CSF Aβ40 with an $ED_{50}$ between 1 mg/kg and 10 mg/kg.

Subchronic Rat Studies

Based on the effects of (2R)-2-[[(4-chlorophenyl)sulfonyl][[2-fluoro-4-(1,2,4-oxadiazol-3-yl)phenyl]methyl]amino]-5,5,5-trifluoropentanamide on rat brain Aβ40 described in the previous section, rats were administered daily doses of 3, 10, 30 or 100 mg/kg/day. Animals were euthanized 12 or 24 hours after the third dose or 5 hours after the fourth dose. Brain Aβ40 AUC reductions were estimated by linear extrapolation of values obtained from animals after 5, 12, or 24 hours of dosing within the same dose group as shown in Table 2. Based on this analysis, Aβ40 AUC reductions averaged 53% at 3 mg/kg/day and increased to greater than 85% at doses of 10 mg/kg/day or higher. Compound levels were measured at several times to estimate compound AUC (0-24 hr) values at the beginning and end of the experiment. These values showed that compound exposures after 3 doses were within 2-fold of exposures after the initial dose. Histological evaluation of the duodenal tissue from these rats showed that ⅓ rats dosed with 100 mg/kg/day had mild lesions.

TABLE 2

Summary of Results from 4-day Rat Studies

| Study | Dose (mg/kg/day) | Compound PK AUC (uM · h) (ng · h/mL) plasma | | Terminal Brain Abeta 40 (% Veh)[a] | | | Brain[b] % Aβ AUC Reduction | GI Tox |
|---|---|---|---|---|---|---|---|---|
| | | Day 1[c] | End[d] | 5 hr | 12 hr | 24 hr | | |
| No. 1 (N = 3) | 3 | 10 5200 | 12 6240 | 39% | 35% | 92% | 49% | NAD |
| | 10 | 60 31200 | 48 24960 | 12% | 9% | 28% | 85% | NAD |
| | 30 | 169 87880 | 93 48360 | 8% | 9% | 13% | 90% | NAD |

TABLE 2-continued

Summary of Results from 4-day Rat Studies

| Study | Dose (mg/kg/day) | Compound PK AUC (uM · h) (ng · h/mL) plasma | | Terminal Brain Abeta 40 (% Veh)[a] | | | Brain[b] % Aβ AUC Reduction | GI Tox |
|---|---|---|---|---|---|---|---|---|
| | | Day 1[c] | End[d] | 5 hr | 12 hr | 24 hr | | |
| No. 2 (N = 3) | 3 | 10 5200 | 13 6760 | 16% | 34% | 94% | 57% | NAD |
| | 10 | 65 33800 | 55 28600 | 6% | 4% | 23% | 91% | NAD |
| | 30 | 191 99320 | 116 60320 | 6% | 4% | 15% | 93% | NAD |
| | 100 | 328 170560 | 199 103480 | 3% | 3% | 7% | 96% | +[e] |

[a]Values represent mean brain Aβ40 levels from n = 3 animals expressed relative to the average of the vehicle control group
[b]Brain Aβ40 AUC reductions were estimated by linear extrapolation of values obtained from animals after 5, 12 or 24 h of dosing within the same dose group
[c]Values represent mean AUC (uM · h or ng · h/mL) from n = 3 animals. AUCs were estimated from samples taken at 5, 12, and 24 h post dose 1 (Study No. 1) or from samples taken at 5, 12, 17, and 24 h post dose 1 (Study No. 2)
[d]Values represent mean AUC (uM · h or ng · h/mL) from n = 3 animals. AUCs were estimated from samples taken at 12 and 24 h post dose 3 and 5 h post dose 4 (Study No. 1) or from samples taken at 12 and 17 and 24 hours post dose 3 and 5 hours post dose 4 (Study No. 2)
[e]Goblet cell metaplasia noted in 1 of 3 animals
NAD = no abnormalities detected Results from subchronic rat studies showed that (2R)-2-[[(4-chlorophenyl)sulfonyl][[2-fluoro-4-(1,2,4-oxadiazol-3-yl)phenyl]methyl]amino]-5,5,5-trifluoropentanamide reduced brain Aβ40 without GI toxicity. In particular, a 3 mg/kg/day dose caused an approximately 50% brain Aβ40 AUC reduction compared to a 100 mg/kg/day dose needed to induce GI toxicity.

Microscopic evaluation of the proximal duodenum in a single animal in the high dose group (1 of 3 animals evaluated at this dose level) given 100 mg/kg/day of (2R)-2-[[(4-chlorophenyl)sulfonyl][[2-fluoro-4-(1,2,4-oxadiazol-3-yl)phenyl]methyl]amino]-5,5,5-trifluoropentanamide once daily for 4 days revealed a slight goblet cell metaplasia in that animal. No drug-related duodenal changes were noted in rats given (2R)-2-[[(4-chlorophenyl)sulfonyl][[2-fluoro-4-(1,2,4-oxadiazol-3-yl)phenyl]methyl]amino]-5,5,5-trifluoropentanamide at ≦30 mg/kg.

In another experiment, rats were dosed daily for either 4 or 7 days with 30 mg/kg/day or 300 mg/kg/day (Table 3). Brain Aβ40 levels at termination (5 hours post dose) were 13% of the vehicle control and thus similar to previous rat studies with (2R)-2-[[(4-chlorophenyl)sulfonyl][[2-fluoro-4-(1,2,4-oxadiazol-3-yl)phenyl]methyl]amino]-5,5,5-trifluoropentanamide. Compound plasma levels were similar 5 hours after the first and fourth dose. Some rats in the 300 mg/kg/day dose group (4 of 5) showed GI toxicity after 4 days of dosing, but none of the rats in the other treatment groups had detectable GI toxicity, including animals dosed for 7 days.

TABLE 3

Summary of Results from Rat Study No. 3

| Dose[a] (mg/kg/day) | Plasma Conc. 5 hr post dose (uM) | | Day 4 GI Tox | Plasma Conc. 5 hr post dose (uM) | | Day 7 5 hr Brain Aβ40 (% Veh) | GI Tox |
|---|---|---|---|---|---|---|---|
| | Day 1 | Day 4 | | Day 1 | Day 7 | | |
| 30 | 5.9 | 5.6 | NAD | 7.2 | 6.2 | 13% | NAD |
| 300 | 12 | 10 | +[b] | 14 | 11 | 13% | NAD |

[a]N = 5 animals/dose group/terminal time point (Day 4 or Day 7) were tested
[b]Goblet cell metaplasia noted in 4 of 5 animals.
NAD = no abnormalities detected The above results confirm that (2R)-2-[[(4-chlorophenyl)sulfonyl][[2-fluoro-4-(1,2,4-oxadiazol-3-yl)phenyl]methyl]amino]-5,5,5-trifluoropentanamide is a potent and selective γ-secretase inhibitor. These results support the use of (2R)-2-[[(4-chlorophenyl)sulfonyl][[2-fluoro-4-(1,2,4-oxadiazol-3-yl)-phenyl]methyl]amino]-5,5,5-trifluoropentanamide as a therapeutic treatment for Alzheimer's disease and other disorders associated with β-amyloid peptide.

The following examples are given by way of illustration and are not to be construed as limiting the invention in any way inasmuch as variations of the invention are possible within the spirit of the invention.

The compounds of the present application can be prepared in a number of ways well known to one skilled in the art of organic synthesis. The compounds of the present application can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The compounds may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

DESCRIPTION OF THE SPECIFIC EMBODIMENTS

In the following examples, all temperatures are given in degrees Centigrade. Melting points were recorded on a Thomas Scientific Unimelt capillary melting point apparatus and are uncorrected. Proton magnetic resonance ($^1$H NMR) spectra were recorded on a Bruker Avance 300, a Bruker Avance 400, or a Bruker Avance 500 spectrometer. All spectra were determined in the solvents indicated and chemical shifts are reported in δ units downfield from the internal standard tetramethylsilane (TMS) and interproton coupling constants are reported in Hertz (Hz). Multiplicity patterns are designated as follows: s, singlet; d, doublet; t, triplet; q, quartet; m, multiplet; br, broad peak; dd, doublet of doublet; br d, broad doublet; dt, doublet of triplet; br s, broad singlet; dq, doublet of quartet. Infrared (IR) spectra using potassium bromide (KBr) or sodium chloride film were determined on a Jasco FT/1R-410 or a Perkin Elmer 2000 FT-IR spectrometer from 4000 cm$^{-1}$ to 400 cm$^{-1}$, calibrated to 1601 cm$^{-1}$ absorption of a polystyrene film and reported in reciprocal centimeters (cm$^{-1}$). Optical rotations $[\alpha]_D$ were determined on a Rudolph Scientific Autopol IV polarimeter in the solvents indicated; concentrations are given in mg/mL. Low resolution mass spectra (MS) and the apparent molecular (MH$^+$) or (M–H)$^+$ was determined on a Finnegan SSQ7000. High resolution mass spectra were determined on a Finnegan MAT900. Liquid chromatography (LC)/mass spectra were run on a Shimadzu LC coupled to a Water Micromass ZQ.

The following abbreviations are used: DMF (dimethylformamide); THF (tetrahydrofuran); DMSO (dimethylsulfoxide), Leu (leucine); TFA (trifluoroacetic acid); MTBE (methyltertbutylether); DAST [(diethylamino)sulfur trifluoride], HPLC (high pressure liquid chromatography); rt (room temperature); aq. (aqueous); AP (area percent).

Preparation A (R)-2-Amino-5,5,5-trifluoropentanamide hydrochloride

Step A. 4,4,4-Trifluorobutanal

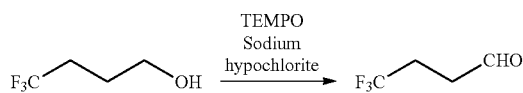

Dichloromethane (4.2 L) was charged into a 20 L four necked round bottom flask, equipped with mechanical stirring and cooling bath. The stirring was started and the reaction mixture cooled to 0 to –2° C. 4,4,4-Trifluorobutanol (750.0 g) was charged and the reaction mixture was cooled further to –5 to –8° C. TEMPO; (2,2,6,6-tetramethyl-1-piperidinyloxy, free radical) (9.15 g) was added while keeping the temperature between –5 to –8° C. An aqueous solution of potassium bromide (60 g in 1.17 L of water) was added to the above solution and the temperature was maintained at –5 to –8° C. An aqueous solution of NaOCl (8.8 L, 6-7% by wt., buffered to pH 8.5 using sodium bicarbonate) was added to the reaction mixture (caution: exothermic) while keeping the temperature of the reaction mixture at –5° C. Similarly, sodium periodate (NaIO$_4$) can substitute for NaOCl as the oxidizing agent. After complete addition, the dichloromethane layer was separated and the aqueous layer was washed with dichloromethane (1×750 mL). The dichloromethane layers were combined and dried using anhydrous sodium sulfate. The drying agent was filtered, and concentration of the solution of 4,4,4-trifluorobutanal was determined by NMR. The solution containing the title compound was used directly in the next step without additional processing. $^1$H NMR (CDCl$_3$) (400 MHz) δ 2.30-2.50 (m, 2H, CH$_2$—CF$_3$), 2.70-2.80 (m, 2H, CH$_2$—CHO), 9.8 (s, 1H, CHO).

Step B. 5,5,5-Trifluoro-2-(1-phenylethylamino)pentanenitrile (mixture of diastereomers)

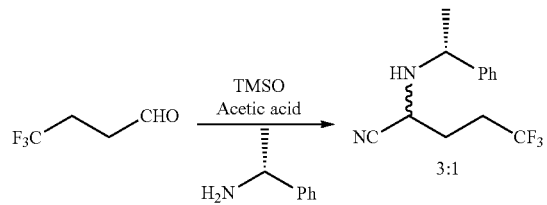

R-α-Methyl benzyl amine (528.5 g) was charged into a suitable vessel equipped with mechanical stirring, cooling bath and maintained under a blanket of nitrogen. 4,4,4-Trifluorobutyraldehyde solution (from Step A, 550 g) was charged, followed by methanol (3.3 L). The reaction mixture was then cooled to about 0 to –3° C. Acetic acid (glacial, 260 mL) was added drop-wise, maintaining the temperature around 0° C. followed by trimethylsilyl cyanide (581 mL) over a period of 15 minutes. Similarly, sodium cyanide (NaCN) or potassium cyanide could be used as the cyanide source. The reaction mixture was warmed to 25 to 27° C. and stirred overnight. Completion of the reaction was determined by TLC. Chilled Water (10.0 L) was charged into the reaction mixture and the reaction mixture was extracted with dichloromethane (1×10.0 L). The dichloromethane layer was washed with water (2×10.0 L) followed by brine (1×5.0 L). The dichloromethane layer was dried over anhydrous sodium sulfate and concentrated under reduced pressure to yield the title aminonitrile (mixture of diastereomers) as a viscous liquid, average yield 90%. $^1$H NMR (CDCl$_3$) (400 MHz) δ

1.42 (d&m, 5H), 2.15 & 2.35 (two m, 1H each), 3.10-3.20 (m, 1H), 4.10-4.15 (m, 1H), 7.10-7.35 (m, 6H).

Step C.
5,5,5-Trifluoro-2-(1-phenylethylamino)pentanamide (mixture of diastereomers)

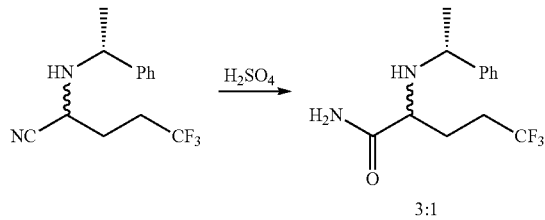 [SMILES: C[C@@H](NC(C#N)CCC(F)(F)F)c1ccccc1 ; "H2SO4" ; C[C@@H](NC(CCC(F)(F)F)C(N)=O)c1ccccc1]

3:1

5,5,5-Trifluoro-2-(1-phenylethylamino)pentanenitrile (crude mixture of diastereomers from Step B, 1.10 kg) was dissolved in dichloromethane (5.5 L) in a suitable vessel equipped with mechanical stirring, ice bath for cooling and maintained under a blanket of nitrogen. Stirring was started and the reaction mixture was cooled to 0 to −5° C. Concentrated sulfuric acid (1.75 L) was added dropwise over a period of 1 hour into the above mixture, maintaining the temperature below 0° C.; a clear solution was obtained after the addition was complete. The temperature of the reaction mixture was raised to 25 to 27° C. and stirred overnight (12-14 h). Completion of the reaction was determined by HPLC. The reaction mixture was poured slowly over crushed ice (~15.0 kg) and was neutralized with aqueous ammonia (~25% by volume). The aqueous layer was separated and extracted with dichloromethane (2×3.0 L). The combined dichloromethane layer was washed with water (1×12.0 L) followed by brine (1×3.0 L). The product rich organic layer was dried over sodium sulfate and concentrated under reduced pressure to yield 0.85 kg (72.0%) of the crude title compound $^1$H NMR (CDCl$_3$) (400 MHz) (Mixture of diasteromers) δ 1.36 (d&m, 4H-1, CH$_3$ (J=8.0 Hz & 1H of CH$_2$), 1.90 (m, 1H of CH$_2$), 2.15 & 2.35 (two m, 1H each of CH$_2$—CF$_3$), 2.80-2.90 (m, 1-H, CH-Ph), 3.60-3.70 (m, 1H, —(CONH$_2$)CH(NH), 5.90 & 6.45 (1H each of CONH$_2$ with minor peaks for other diasteromer), 7.20-7.40 (m, 6H, Ar+NH).

Step D. (R)-5,5,5-Trifluoro-2-((R)-1-phenylethylamino)pentanamide hydrochloride

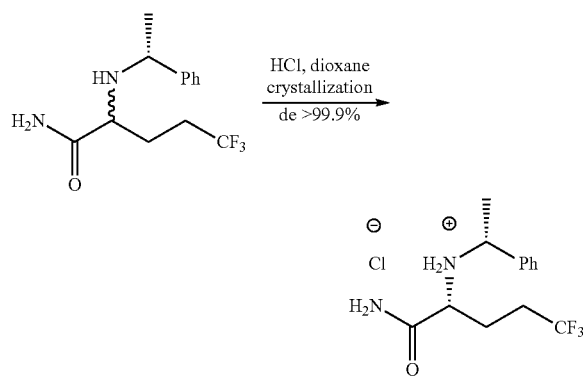

5,5,5-Trifluoro-2-(1-phenylethylamino)pentanamide (mixture of diastereomers) (850 g) was charged into a suitable vessel equipped with mechanical stirring and cooling bath. Methanol (2.55 L), ethyl acetate (1.7 L) and water (1.06 L) were charged and the reaction mixture was cooled to 0 to 5° C. A solution of HCl in dioxane (4.5 M, 1.72 L) was added dropwise over a period of 30 to 45 minutes. Similarly, mixtures of isopropanol and methyl tert-butyl ether could be used as solvent, and aqueous or concentrated HCl could be used as the HCl source. The temperature of the reaction mixture was then raised to 25 to 27° C. and stirred for 2 hours. Completion of the reaction was determined by TLC. The solid that precipitated was filtered and the cake was washed with a suitable solvent, such as ethyl acetate (1.8 L) followed by petroleum ether (2.5 L), or a mixture of isopropanol and methyl tert-butyl ether. The solid was allowed to dry at ambient temperature in an open tray, giving the title R-amino amide (480 g, 50% yield, diastereomeric excess=99.9%) $^1$H NMR (CDCl$_3$) (400 MHz) δ 1.73 (d, 3H, CH$_3$, 0.1=8.0 Hz), 2.08-2.09 (m, 2H of CH$_2$), 2.20-2.40 (m, 2H, CH$_2$—CF$_3$), 3.50-3.55 (m, 1H, CH-Ph), 4.40-4.41 (m, 1H, —(CONH$_2$)CH(NH), 7.48-7.53 (br s, 5H, Ar).

Step E. (R)-2-Amino-5,5,5-trifluoropentanamide hydrochloride

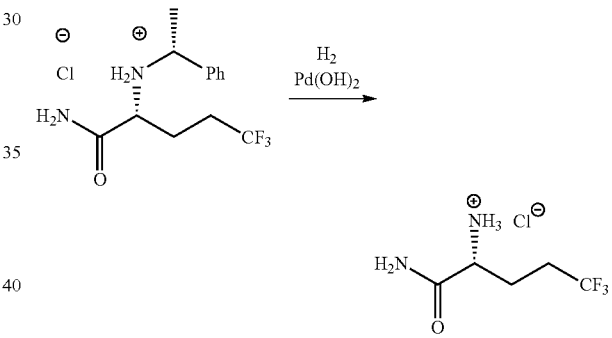

To a suitable pressure vessel, (R)-5,5,5-trifluoro-2-((R)-1-phenylethylamino)-pentanamide hydrochloride (1.50 kg) was charged along with methanol (15.0 L). This was followed by the addition of water (701.0 mL) followed by 20% palladium hydroxide on carbon (225 g). Similarly, palladium on carbon (Pd/C) could be used as the hydrogenation catalyst. The vessel was flushed with nitrogen three times, and then hydrogen gas was pressurized into the vessel (3-4 kg/cm2) at 60° C. The reaction was monitored for completion by HPLC. Upon completion, the reaction mixture was allowed to cool to 30-35° C. and filtered through a Celite pad, then washed with methanol. The filtrate was then concentrated under reduced pressure. After complete concentration, the remaining reaction mixture was treated with dichloromethane (2.5 L per wash), filtered and dried at 45° C. for 12 hours, giving the title compound (915 g, 91.0%; Purity=97%). $^1$H NMR (DMSO-d$_6$) (400 MHz) δ 2.00 (m, 2H, CH$_2$), 2.30-2.40 (m, 2H of CH$_2$—CF$_3$), 3.85-3.88 (m, 1H, —(CONH$_2$)CH(NH), 7.64 & 8.11 (br s, 1H, each of CONH$_2$), 8.44 (br s, 3H, $^{13}$C NMR (DMSO-d$_6$) (100.0 MHz) δ 169.57, 131.20, 128.45, 125.71, 122.97, 50.91, 29.46, 29.18, 28.89, 28.61, 23.56, 23.53.

Preparation B (R)-5,5,5-Trifluoronorvaline

Method A. R-Transaminase (Biocatalytics and BMS Transaminases)

A solution containing 5,5,5-trifluoro-2-oxopentanoic acid (100 mg, 0.588 mmoles), R,S-alanine (200 mg, 2.244 mmoles), and 0.02 mM pyridoxal phosphate, in 0.1 M potassium phosphate buffer, pH 7.5, was incubated with R-transaminase AT-103 from Biocatalytics (5 mg, 44 units) or cloned R-transaminase from *Bacillus thuringiensis* SC16569 (0.5 mL, 10 units, BMS transaminase) at 30° C. in a total volume of 5 mL in 15 mL tubes for 44 h. Reaction yields of (R)-5,5,5-trifluoro-2-aminopentanoic acid of 49% and 48% were obtained with AT-103 and BMS transaminases, respectively. Ee was 100% in both cases.

The yields were increased by adding auxiliary enzymes to reduce pyruvate to lactate. Lactate dehydrogenase requires NADH as a cofactor. The NADH was regenerated using formate dehydrogenase. A solution containing 5,5,5-trifluoro-2-oxopentanoic acid (100 mg, 0.588 mmoles), D,L-alanine (200 mg, 2.244 mmoles), 0.02 mM pyridoxal phosphate, sodium formate (68 mg, 1 mmole), NAD (3.31 mg, 5 μmoles) L-lactate dehydrogenase cloned from rabbit muscle (Biocatalytics LDH-103, 0.107 mg, 15 units), and formate dehydrogenase (0.5 mL, 15 units cloned from *Pichia pastoris* and expressed in *Escherichia coli*) in 0.1 M potassium phosphate buffer, pH 7.5, was incubated with R-transaminase AT-103 from Biocatalytics (5 mg, 44 units) or cloned R-transaminase from *Bacillus thuringiensis* SC16569 (0.5 mL, 10 units) at 30° C. in a total volume of 5 mL in 15 mL tubes. Reaction yields of (R)-5,5,5-trifluoro-2-aminopentanoic acid of 94% and 91% were obtained with AT-103 and BMS transaminases, respectively. Ee was 100% in both cases.

Method B. (R)-Amino Acid Dehydrogenase (Biocatalytics and BMS)

Procedure 1: 5,5,5-trifluoro-2-oxopentanoic acid (60.00 g, 0.353 moles), NH$_4$Cl (64.19 g, 1.2 moles), glucose (86.4 g, 0.479 moles) and water (975 mL) were charged to a 2-L jacketed reactor. NaOH (36 mL of 10 N) was added and the mixture was stirred with a magnet at 30° C. to dissolve the solids. The pH was about 7. Na$_2$CO$_3$ (12.72 g, 0.12 moles) was added which brought the pH to about 8.5. NADP (458 mg, 0.60 mmoles), glucose dehydrogenase (33.7 mg, 5277 units from Amano Enzyme Company), and R-amino acid dehydrogenase (600 mg D-AADH-102, from Biocatalytics) were then added in that order. The reaction mixture was brought to pH 9 by dropwise addition of 10 N NaOH. The reaction mixture was stirred at 30° C. and maintained at pH 9.00 by addition of 5 N NaOH from a pH stat. After 21 h the solution yield of (R)-5,5,5-trifluoro-2-aminopentanoic acid was 51.1 g, 84.7% yield, 100% ee.

Procedure 2: 5,5,5-trifluoro-2-oxopentanoic acid (60.00 g, 0.353 moles), NH$_4$Cl (64.19 g, 1.2 moles), glucose (86.4 g, 0.479 moles) and water (975 mL) were charged to a 2-L jacketed reactor. NaOH (36 mL of 10 N) was added and the mixture was stirred with a magnet at 30° C. to dissolve the solids. The pH was about 7. Na$_2$CO$_3$ (12.72 g, 0.12 moles) was added which brought the pH to about 8.5. NADP (458 mg, 0.60 mmoles), glucose dehydrogenase (33.7 mg, 5277 units from Amano Enzyme Company), and D-amino acid dehydrogenase (50 mL extract containing 1500 units, BMS enzyme) were then added in that order. The reaction mixture was brought to pH 9 by dropwise addition of 10 N NaOH. The reaction mixture was stirred at 30° C. and maintained at pH 9.00 by addition of 5 N NaOH from a pH stat. After 15 h the solution yield of (R)-5,5,5-trifluoro-2-aminopentanoic acid was 51.04 g, 84.6% yield, 99.1% ee.

Preparation C 4-(Bromomethyl)-3-fluorobenzonitrile

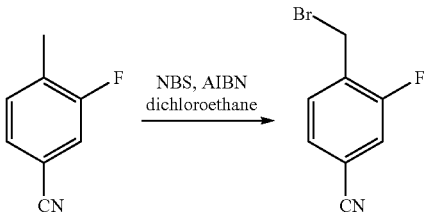

Method A. NBS/AIBM Bromination 1,2-Dichloroethane (151 kg) was charged to a suitable vessel along with 4-cyano-2-fluorotoluene (24 kg) and AIBN (2 kg). The mixture was heated to 70-74° C. Once the batch temperature reached 70° C., N-bromosuccinimide (47.4 kg) was added in portions at the rate of 12 kg/h, maintaining the temperature at 70–74° C. (it is important to control addition rate to avoid exothermic reaction). The mixture was sampled via GC detection after 24 kg of N-bromosuccinimide was added, and the reaction was heated at 70-74° C. until complete reaction was observed. The mixture was cooled to 0-5° C. and allowed to stand for 2 additional hours. The mixture was filtered, and the cake was washed with MTBE (24 kg). The filtrate was washed with water (3×65 kg). The organic layer was dried with sodium sulfate (10.3 kg) for 6 hours, filtered and the cake was washed with MTBE (24 kg). The solution was evaporated under reduced pressure, ethanol (12 kg) was added and the mixture was heated to 40-45° C., then cooled slowly to 0-5° C. while stirring to crystallize. The mixture was filtered and the cake was washed with cold ethanol (5 kg). The crude solid was recrystallized from petroleum ether, filtered and washed with petroleum ether (10 kg), giving the title compound 4-(bromomethyl)-3-fluorobenzonitrile as an off white solid (21 kg, 55% yield). $^1$H NMR (300 MHz, CDCl$_3$) δ ppm 4.46-4.50 (m, 2H) 7.36 (dd, J=8.85, 1.32 Hz, 1H) 7.44 (dd, J=7.91, 1.32 Hz, 1H) 7.52 (dd, J=7.91, 7.16 Hz, 1H). $^{13}$C NMR (75 MHz, CDCl$_3$) δ ppm 23.65 (d, J=4.60 Hz, 1C) 113.76 (d, J=9.77 Hz, 1C) 117.09 (d, J=2.87 Hz, 1C) 119.44 (d, J=24.71 Hz, 1C) 128.44 (d, J=4.02 Hz, 1C) 130.66-130.81 (s, 1C) 130.81-131.06 (s, 1C) 132.18 (d, J=3.45 Hz, 1C) 159.86 (d, J=254.03 Hz, 1C). IR: (KBr) 3088, 3077, 3040, 2982, 2250, 1571, 1508, 1439, 1248 cm$^{-1}$.

Anal. Calcd for C$_8$H$_5$BrFN: Calc. C, 44.89; 1-1, 2.35; N, 6.54; F, 8.88. Found: C, 44.94; H, 2.73; N, 6.56; F, 8.73.

Method B. Sodium Bromate Bromination

To a suitable reactor was added dichloromethane (40 L) and 3-fluoro-4-methylbenzonitrile (4 kg, 18.7 mol) followed by a solution of sodium bromate in water (13.45 kg, 89.1 mol dissolved in 53.6 L water). The reaction mixture was cooled to 0-5° C. A solution of sodium bisulfite (9.25 kg dissolved in 42 L water) was added over a period of 2-3 hours while maintaining a batch temperature of 10-20° C. (the reaction is exothermic). After the addition was complete, a 200 W lamp was shined on the reactor and the batch temperature was increased to 25-30° C. The light and temperature were continued until product was 70-75% by HPLC. The light was removed, stirring was stopped and the reaction was permitted to settle for 15 minutes. The organic layer was removed and the remaining aqueous layer was extracted with dichloromethane twice. The organic layers were combined and washed four times with 10% sodium thiosulfate solution. The organic layer was then washed with brine (10 L) and dried with sodium sulfate. The organic layer was concentrated and then petroleum ether was added and distilled to dryness twice to remove all dichloromethane. Petroleum ether (3 L) was added and the slurry was cooled to 5-10° C. for 1 hour. The slurry was filtered and washed with cold petroleum ether. The product was dried in a vacuum oven at 40-45° C. to give the title compound (3.2 kg, 50.4% yield) as an off-white solid.

Representative procedure for recovery of the title compound from mother liquor: The crude mass (~36% 4-(bromomethyl)-3-fluorobenzonitrile and ~59% gem-dibromide) obtained from concentration of mother liquor (300 g) and 2 equivalents of diisopropyl ethyl amine (based on gem-dibromide) was dissolved in acetonitrile (3 L) and water (50 mL). The reaction was cooled to 0-5° C. and diethyl phosphite (169 g, 1.22 mot) was added over 30 minutes (addition was exothermic). The reaction was stirred for 60-90 min at 0-5° C. and was monitored by TLC. When dibromide was no longer present by TLC, water (3.3 L) was added and the resulting slurry was filtered. The filter cake was washed with water and dried in a vacuum oven (until the moisture content was <1%) to give 202 g (98 AP by HPLC) of additional title compound.

Preparation D

Preparation of 3-fluoro-N'-hydroxy-4-methylbenzimidamide

To a suitable vessel equipped with mechanical stirrer under $N_2$ atmosphere was charged 202.0 g of 3-fluoro-4-methylbenzonitrile followed by 1.0 L of ethanol. Hydroxylamine (144 mL of 50% solution in water) was added via addition funnel over 20 minutes. The mixture was stirred at ambient temperature until HPLC analysis showed that reaction was complete (no starting material remained). Water (3.0 L) was added dropwise to the pale yellow solution over 1 hour to give a thick slurry. The slurry was cooled in an ice water bath to 2° C. for 1.5 hours, filtered and dried under vacuum at 35° C. for 22 hours to give the title compound (230.3 g, 91.6%) as a white solid. $^1$H-NMR (CDCl$_3$, 500 MHz) δ 7.30 (m, 2H), 7.19 (m, 1H), 4.87 (s, 2H), 2.28 (s, 3H); $^{13}$C-NMR (CDCl$_3$, 500 MHz) δ162.15, 160.19, 151.58, 131.82, 131.76, 131.66, 131.62, 127.01, 126.87, 121.06, 112.69, 112.51, 14.48; $^{19}$F-NMR (CDCl$_3$, 500 MHz) δ-116.35, −116.37, −116.39. LC-MS M+H169.19, Preparation E Preparation of 3-(3-fluoro-4-methylphenyl)-1,2,4-oxadiazole Method A. Boron Trifluoride Crude amide oxime 3-fluoro-N'-hydroxy-4-methylbenzimidamide (118.6 g) and triethyl orthoformate (292 mL, 260 g, 1.76 mol) were slurried in dichloromethane (800 mL) and boron trifluoride diethyl etherate (14.8 mL, 16.6 g, 0.12 mol) was added at room temperature. The resulting yellow solution was heated to 45° C. for 1 hour and held at room temperature for 16 hours, which provided 60% conversion by HPLC. The solution was heated to 45° C. for 2.5 hours which brought the conversion to ~1% residual starting material. After cooling to room temperature, 1N HCl (600 mL) was added to the mixture. The phases were separated, and the aqueous layer was extracted with dichloromethane (200 mL). The combined organic layer was dried over sodium sulfate and concentrated at 25° C. under reduced pressure to provide a white solid. Drying under high vacuum for 16 hours provided the title compound (102.3 g, 98% yield over two steps).

Method B. Trifluoroacetic Acid

A suitable vessel equipped with a mechanical stirrer under a $N_2$ atmosphere was charged with 3-fluoro-N'-hydroxy-4-methylbenzimidamide (302.52 g, 1.79 mol), triethyl orthoformate (382.5 mL, 341.1 g, 2.3 mol) and acetonitrile (1512 mL). The reaction mixture was heated to 45° C. and trifluoroacetic acid (6.72 mL, 10.08 g, 87.6 mmol) was added at this temperature. The reaction mixture was heated at 60° C. for an additional 90 minutes, then cooled to room temperature. Water (3 L) was added dropwise over a period of 60 minutes. The slurry was cooled to 4° C. and stirred at this temperature for 30 minutes. The solid was filtered and dried in vacuum at 50° C. for 12 hours to give 3-(3-fluoro-4-methylphenyl)-1,2,4-oxadiazole as a white solid (306 g, 95.6%). HPLC indicated 99.8% chemical purity. $^1$H-NMR (CDCl$_3$, 400 MHz) δ 8.67 (s, 1H), 7.71 (m, 2H), 7.23 (t, 0.1=8 HZ, 1H), 2.28 (s, 3H); $^{13}$C-NMR (CDCl$_3$, 400 MHz) δ 166.9447, 164.7258, 162.5473, 160.1066, 132.0480, 132.0077, 128.5987, 122.9910, 122.9507, 114.2568, 114.0147, 14.6902. $^{19}$F-NMR (CDCl$_3$, 400 MHz) δ-115.94, −115.96.

Anal, Calcd for $C_9H_7N_2O$: C, 60.67; H, 3.96; N, 15.72. Found: C, 60.54; H, 3.78; N, 15.69.

Preparation F

Preparation of 3-(4-(bromomethyl)-3-fluorophenyl)-1,2,4-oxadiazole

Method A. Stepwise Bromination

To a stirring mixture of 3-(3-fluoro-4-methylphenyl)-1,2,4-oxadiazole (5.34 g, 30 mmol), CCl$_4$ (50 mL) and NBS (11.7 g, 66 mmol) was added AIBN (246 mg, 1.5 mmol). The reaction mixture was heated to 80° C. for 3 hour under nitrogen, cooled to room temperature, and 50 mL of saturated sodium bicarbonate solution was added. The organic layer was separated and the aqueous layer was extracted with dichloromethane (50 mL). The organic layer was dried over sodium sulfate, filtered and concentrated on a rotovap to give 3-(4-(dibromomethyl)-3-fluorophenyl)-1,2,4-oxadiazole, (9.34 g, 93%) as a white solid which was used in the next step without further purification. A 200 mL round bottom flask was charged with 3-(4-(dibromomethyl)-3-fluorophenyl)-1,2,4-oxadiazole (8.37 g, 25 mmol) and THF (60 mL). The mixture was cooled to 0° C. and diisopropyl ethyl amine (3.48 g, 27 mmol) was added dropwise over 15 minutes, followed by diethyl phosphite (3.7 g, 26.8 mmol). The mixture was stirred at room temperature for 60 minutes and quenched with 40 mL of water. The aqueous layer was extracted with ether (2×80 mL). The combined organic layer was washed with 20 mL of sat aq. NH$_4$Cl and 20 mL of saturated sodium chloride solution. The organic layer was dried over sodium sulfate, filtered and concentrated on a rotovap to give a crude solid which was purified by a short silica pad to afford 3-(4-(bromomethyl)-3-fluorophenyl)-1,2,4-oxadiazole (6.03 g, 94%). mp 87.3° C. $^1$H-NMR (CDCl$_3$, 400 MHz) δ 8.80 (s, 1H), 7.94 (dd, 1H), 7.87 (dd, 1H), 7.58 (t, 1H), 4.57 (s, 2H); $^{13}$C-NMR (CDCl$_3$, 400 MHz) δ 166.97, 166.95, 165.45, 162.29, 159.73, 132.34, 132.30, 128.99, 128.90, 128.81, 124.04, 124.01, 115.56, 115.32, 25.22, 25.18; $^{19}$F-NMR (CDCl$_3$, 400 MHz) δ −115.81, −115.84, −115.86. Anal. Calcd for $C_9H_6BrFN_2O$: C, 42.05; H, 2.35; N, 10.90. Found: C, 42.17; H, 2.17; N, 10.63.

Method B. Alternative One-Pot Bromination 3-(3-Fluoro-4-methylphenyl)-1,2,4-oxadiazole (101.8 g, 0.57 mol) and N-bromosuccinimide (206 g, 1.16 mol) were dissolved in acetonitrile (~1 L) and azobisisobutyronitrile (4.2 g, 26 mmol) was added at room temperature. The mixture was heated to 70° C. for 2 hours at which point HPLC showed complete conversion of the starting material to a mixture of the monobromide and dibromide. The mixture was cooled to 0° C. and diisopropyl ethyl amine (73 mL, 54.2 g, 0.42 mol) was added while maintaining the reaction temperature below 5 C. Diethyl phosphite (54.7 mL, 58.6 g, 0.42 mol) was added slowly and the reaction mixture was warmed to room temperature. After 2 hours HPLC showed complete conversion of the dibromide to the monobromide. Water (1.2 L) was added and the resulting precipitate was filtered. Washing with water (2×200 mL) and drying provided 3-(4-(bromomethyl)-3-fluorophenyl)-1,2,4-oxadiazole (135 g, 92% yield).

Method C: Sodium Bromate Bromination (Direct Isolation)

Sodium bromate (2.54 g) was dissolved in water (8.4 mL). To this solution was added a solution of 3-(3-fluoro-4-methylphenyl)-1,2,4-oxadiazole (1.0 g) in EtOAc (12 mL) at rt. A solution of $NaHSO_3$ (1.75 g) in water (17 mL) was added dropwise (CAUTION: EXOTHERMIC). The mixture was stirred at rt for 2 h, and then kept in a cold room overnight. The organic layer was separated, washed with 10% $Na_2S_2O_3$ and water, and then concentrated. The resulting solid was dissolved in EtOAc (~6 mL). Heptane was added slowly (~30 mL). The slurry was stirred at rt for 3 h, and then filtered. The solid was washed with heptane (15 mL), then dried giving 0.74 g (51%) of the title compound: HPLC: 99.42AP. Second crop recovery: the filtrate was concentrated to a volume ~30 mL and the resulting slurry was filtered to give the title compound as a white solid 0.23 (16%) with HPLC 97.09 AP.

Method D: Sodium Bromate Bromination (Two Step Procedure Using Reduction of Dibromide)

A solution of 3-(3-fluoro-4-methylphenyl)-1,2,4-oxadiazole (20.0 g, 112.2 mmol) in dichloromethane (200 mL) was added to a solution of $NaBrO_3$ (50.8 g, 336.7 mmol) in water (200 mL) at rt. The resulting two-phase mixture was cooled to 0° C. The solution of $NaHSO_3$ (35.7 g, 336.7 mmol) in water (160 mL) was added dropwise to maintain the batch temperature below 20° C. (~1 h), The resulting red solution was stirred at rt until 3-(3-fluoro-4-methylphenyl)-1,2,4-oxadiazole was below 1.0 AP by HPLC (~2 h). The organic layer (bottom layer) was separated, and the aqueous layer was extracted with dichloromethane (200 mL). The combined dichloromethane solution was washed with 10% aqueous $Na_2S_2O_3$ solution (200 mL), water (200 mL) and 15% brine (200 mL). A white solid (a mixture of monobromide and dibromide) was obtained after concentrating under vacuum. This solid was dissolved in wet MeCN (200 mL, KF: 1.5-4%), and the solution was cooled to −5° C. to 0° C. N,N-diisopropylethylamine (6.0 g, 8.1 mL, 46.4 mmol) was added, followed by dropwise addition of diethyl phosphite (6.0 g, 46.1 mmol) over 15 minute. The mixture was stirred at −5° C. to 0° C. until 3-(4-(dibromomethyl)-3-fluorophenyl)-1,2,4-oxadiazole was <0.5 AP (1.5-2 h). Water (500 mL) was added over 30 min, resulting in a white slurry. This slurry was stirred at rt for 1-3 h, and then filtered. The cake was washed with water (2×200 mL), and then dried under vacuum at 45° C. for 20 h.

Anal. Calcd. for $C_9H_6BrFN_2O$: Calc. C, 42.05; H, 2.35; N, 10.89; Br, 31.08; F, 7.39. Found: C, 42.10; H, 2.24; N, 10.90; Br, 31.18; F, 7.00.

EXAMPLE 1

(2R)-2-[[(4-Chlorophenyl)sulfonyl][[2-fluoro-4-(1,2,4-oxadiazol-3-yl)phenyl]methyl]amino]-5,5,5-trifluoropentanamide Step A. 5,5,5-Trifluoro-2-(1-phenylethylamino)pentanenitrile To a solution of (R)-phenethylamine (9.60 g, 79.4 mmol) and acetic acid (5.08 g, 79.6 mmol) in MeOH (150 mL) was added NaCN (3.88 g, 79.6 mmol). The reaction was cooled to 0° C. and a solution of 4,4,4-trifluorobutyraldehyde (10.0 g, 79.6 mmol) in MeOH (50 mL) was added. The reaction was warmed to room temperature and stirred for 20 h. The reaction was diluted with water (400 mL) and extracted with $CH_2Cl_2$ (3×300 mL). The combined organic layer was dried over $Na_2SO_4$ and concentrated under vacuum to provide the aminonitrile title compound (18.1 g, 89%, as a 4:1 mixture of diastereomers) as a pale yellow oil: $^1H$ NMR (300 MHz, $CD_3OD$) δ 7.38-7.27 (m, 5H), 4.15-4.02 (m, 1H), 3.69 (t, J=7.5 Hz, 0.22H), 3.18 (t, J=7.5 Hz, 0.78H), 2.48-2.26 (m, 1H), 2.25-2.03 (m, 1H), 2.01-1.86 (m, 2H), 1.39 (d, J=6.5 Hz, 2.34H), 1.36 (d, J=6.5 Hz, 0.66H); ESI MS m/z 257 $[C_{13}H_{15}F_3N_2+H]$.

Step B. (R)-5,5,5-Trifluoro-2-((R)-1-phenylethylamino)pentanamide hydrochloride

To a solution of 5,5,5-trifluoro-2-(1-phenylethylamino) pentanenitrile (18.0 g, 70.31 mmol, 4:1 mixture of diastereomers) in $CH_2Cl_2$ (100 mL) was added $H_2SO_4$ (100 mL). The reaction was stirred at room temperature for 22 h, poured onto crushed ice and neutralized with $NH_4OH$. The mixture was extracted with EtOAc (3×500 mL). The combined organic layer was dried over $Na_2SO_4$ and concentrated under vacuum to provide the free base of the title compound as a mixture of diastereomers (18.94 g, 98%) as an orange oil: $^1H$ NMR (300 MHz, $CDCl_3$) δ 7.40-7.18 (m, 5H), 6.78 (br s, 0.23H), 6.50 (br s, 0.77H), 6.00 (br s, 0.77H), 5.81 (br s, 0.23H), 3.82 (q, J=6.5 Hz, 0.23H), 3.70 (q, J=6.5 Hz, 0.77H), 3.14 (t, J=6.0 Hz, 0.23H), 2.86 (t, J=7.0 Hz, 0.77H), 2.35-1.86 (m, 2H), 1.84-1.64 (m, 2H), 1.39 (d, J=6.5 Hz, 0.69H), 1.35 (d, J=6.5 Hz, 2.31H); ESI MS m/z 275 $[C_{13}H_{17}F_3N_2O+H]$.

Hydrochloride Salt

To a solution of the free base of the title compound as a mixture of diastereomers (11.9 g, 43.4 mmol) in $Et_2O$/MeOH (7:1, 40 mL) was added a solution of 1 N HCl in $Et_2O$ (70 mL). The white precipitate formed was re-dissolved by heating the mixture and adding MeOH (to a final ratio of 4:1 $Et_2O$/MeOH). The solution was allowed to cool to room temperature and left to stand overnight. The aminoamide hydrochloride salt of the title compound was isolated as a single diastereomer (3.11 g, 23%) as a white solid: $^1H$ NMR (300 MHz, $CD_3OD$) δ 7.93 (br s, 1H), 7.69 (br s, 1H), 7.54-7.44 (m, 5H), 4.39 (q, J=7.0 Hz, 1H), 3.50 (t, J=6.5 Hz, 1H), 2.29-2.20 (m, 2H), 2.10-2.01 (m, 2H), 2.07 (d, J=7.0 Hz, 3H); ESI MS m/z 275 $[C_{13}H_{17}F_3N_2O+H]$.

Step C. (R)-2-(4-Chlorophenylsulfonamido)-5,5,5-trifluoropentanamide

To a solution of (R)-5,5,5-trifluoro-2-(((R)-1-phenylethylamino)pentanamide hydrochloride (3.10 g, 10.0 mmol) in EtOH (100 mL) was added $Pd(OH)_2$ (350 mg) and water (10 mL). The reaction mixture was hydrogenated (40 psi) for 4 h at 50° C. The reaction was filtered through celite and the filtrate was concentrated under vacuum to afford the intermediate amine hydrochloride as a white solid. To a suspension of the amine in CH₂Cl₂ (100 mL) was added N,N-diisopropylethylamine (5.25 mL, 30.0 mmol) and 4-chlorobenzenesulfonyl chloride (2.53 g, 12.0 mmol). The reaction was stirred at room temperature for 18 h. and diluted with EtOAc (200 mL), washed with NaHCO₃ (250 mL) and brine (250 mL), dried over Na₂SO₄, and concentrated under vacuum. The title compound (2.91 g, 84%) was obtained as a white solid by trituration of the residue with CH₂Cl₂/hexanes (2:1): ¹H NMR (300 MHz, CD₃OD) δ 7.84 (dt, J=8.5, 2.0 Hz, 2H), 7.55 (dt, J=8.5, 2.0 Hz, 2H), 3.85 (dd, J=8.5, 5.0 Hz, 1H), 2.34-2.05 (m, 2H), 1.97-1.68 (m, 21-1); EST MS m/z 345 [C₁₁H₁₂ClF₃N₂O₃S+H].

Step D. (R)-2-(4-chloro-N-(2-fluoro-4-(1,2,4-oxadiazol-3-yl)benzyl)phenylsulfonamido)-5,5,5-trifluoropentanamide To a solution of sulfonamide (R)-2-(4-chlorophenylsulfonamido)-5,5,5-trifluoropentanamide (130 mg, 0.37 mmol) in DMF (2 mL) was added Cs₂CO₃ (241 mg, 0.74 mmol) and 3-(4-bromomethyl-3-fluoro-benzyl)-1,2,4-oxadiazole (257 mg, 0.48 mmol). The reaction was stirred at room temperature for 2 h, diluted with water (50 mL), and extracted with EtOAc (2×50 mL). The combined organic extract was washed with water (2×50 mL) and brine (50 mL) and concentrated under vacuum. The residue was purified by column chromatography (silica gel, 0-55% EtOAc/hexanes) to provide the title oxadiazole compound (92 mg, 45%) as a white solid: mp 66-68° C.; ¹H NMR (500 MHz, CDCl₃) δ 8.77 (s, 1H), 7.90 (dd, J=8.0, 1.5 Hz, 1H), 7.77-7.71 (m, 3H), 7.64 (dd, J=7.5, 7.5 Hz, 1H), 7.51 (d, J=8.5 Hz, 2H), 6.34 (s, 1H), 5.28 (s, 1H), 4.66 (d, J=15.6 Hz, 1H), 4.51 (d, J=15.6 Hz, 1H), 4.39 (dd, J=8.9, 6.3 Hz, 1H), 2.25-1.82 (m, 3H), 1.54-1.47 (m, 1H); ESI MS m/z 521 [C₂₀H₁₇ClF₄N₄O₄S+H]⁺; HPLC 98.9% (AUC), t_R=19.4 min.

EXAMPLE 2

(2R)-2-[[(4-Chlorophenyl)sulfonyl][[2-fluoro-4-(1,2,4-oxadiazol-3-yl)phenyl]methyl]amino]-5,5,5-trifluoropentanamide Step A. 4-(Bromomethyl)-3-fluorobenzonitrile To a solution of 3-fluoro-4-methylbenzonitrile (5.0 g, 0.23 mol) in 100 mL of carbon tetrachloride was added N-bromosuccinimide (4.97 g, 0.28 mol) and AIBN (100 mg, 0.61 mmol) and the mixture was refluxed for six hours. The reaction was cooled and filtered. The filtrate was washed with water, dried over magnesium sulfate, filtered and the solvents were removed under vacuum to afford 5.44 g of the title compound as an off-white solid. ¹H NMR indicated the presence of 20% starting material. ¹H NMR (400 MHz, CDCl₃) for the title compound: δ 7.54-7.30 (m, 3H), 4.83 (s, 2H).

Step B. (R)-2-(4-Chloro-N-(4-cyano-2-fluorobenzyl)phenylsulfonamido)-5,5,5-trifluoropentanamide To a solution of (R)-2-(4-chlorophenylsulfonamido)-5,5,5-trifluoropentanamide (6.88 g, 20.0 mmol) and 4-(bromomethyl)-3-fluorobenzonitrile (6.43 g, 30 mmol) in DMF (35 mL) was added anhydrous Cs₂CO₃ (19.56 g, 60 mmol). The resulting mixture was stirred at room temperature for 45 min. and then diluted with EtOAc (200 mL), washed with water (100 mL×4) and dried over Na₂SO₄. The product was purified by Biotage (40+M column, 3% to 80% EtOAc in hexanes, 651 mL). The title compound was obtained as a white solid (6.50 g, 68.1% yield). ¹H NMR (DMSO-d₆, 400 MHz) δ 7.80-7.88 (m, 3H), 7.70-7.75 (m, 2H), 7.67 (d, 2H, J=8), 7.60 (s, 1H), 7.26 (s, 1H), 4.99 (d, 1H, J=16), 4.68 (d, 1H, J=16), 4.14 (t, 1H, J=8), 1.99-2.17 (m, 2H), 1.80-1.94 (m, 1H), 1.40-1.56 (m, 1H). LC/MS M+H 478.14, 94%.

Step C. (2R)-2-[[(4-Chlorophenyl)sulfonyl][[2-fluoro-4-(1,2,4-oxadiazol-3-yl)phenyl]methyl]amino]-5,5,5-trifluoropentanamide To a solution of (R)-2-(4-chloro-N-(4-cyano-2-fluorobenzyl)phenylsulfonamido)-5,5,5-trifluoropentanamide (6.5 g, 13.6 mmol) in EtOH (70 mL) was added NH₂OH (50% in H₂O, 2.6 mL 40.8 mmol). The resulting mixture was stirred at 80° C. under nitrogen for 1 h and then cooled to rt. The solvents were evaporated under reduced pressure. The residue was dissolved in EtOAc and washed with water and dried over Na₂SO₄. Evaporation of the solvent gave a white solid which was recrystallized from EtOAc and hexanes to afford the intermediate amide oxime as a white solid (6.93 g, quantitative yield). To a mixture of the intermediate (R)-2-(4-chloro-N-(2-fluoro-4-(N'-hydroxycarbamimidoyl)benzyl)phenylsulfonamido)-5,5,5-trifluoropentanamide (6.93 g, 13.6 mmol) and triethyl orthoformate (6.77 mL, 40.8 mmol) in dichloroethane (30 mL) was added BF₃.OEt₂ (0.17 mL, 1.36 mmol). The resulting mixture was stirred at 70° C. for 1 h and then cooled to room temperature. Chromatography (silica gel, biotage, 40+M column, 3% to 80% EtOAc in hexanes, 651 mL) provided the title compound as a white solid. (4.9 g, 69.3% yield).

The above 4.9 g of product was combined with a second lot of 9.8 g of (2R)-2-[[(4-chlorophenyl)sulfonyl][[2-fluoro-4-(1,2,4-oxadiazol-3-yl)phenyl]methyl]amino]-5,5,5-trifluoropentanamide (prepared by the procedure described in Example 1). To the combined lots (14.7 g) was added isopropyl alcohol (75 mL). The mixture was refluxed until almost complete dissolution, and then filtered. The filtrate was stirred at rt for 16 h. and filtered. A white fine crystalline white solid was obtained after drying to a constant mass to afford (2R)-2-[[(4-chlorophenyl)sulfonyl][[2-fluoro-4-(1,2,4-oxadiazol-3-yl)phenyl]methyl]amino]-5,5,5-trifluoropentanamide (13.7 g). ¹H NMR (CDCl₃, 500 MHz) δ 8.77 (s, 1H), 7.90 (dd, J=8.0, 1.5 Hz, 1H), 7.77-7.71 (m, 3H), 7.64 (dd, 0.1-7.5, 7.5 Hz, 1H), 7.51 (d, J=8.5 Hz, 2H), 6.34 (s, 1H), 5.28 (s, 1H), 4.66 (d, J=15.6 Hz, 1H), 4.51 (d, J=15.6 Hz, 1H), 4.39 (dd, J=8.9, 6.3 Hz, 1H), 2.25-1.82 (m, 3H), 1.54-1.47 (m, 1H); ESI MS m/z 521 [C₂₀H₁₇ClF₄N₄O₄S+H]⁺.

EXAMPLE 3

(2R)-2-[[(4-Chlorophenyl)sulfonyl][[2-fluoro-4-(1,2,4-oxadiazol-3-yl)phenyl]methyl]amino]-5,5,5-trifluoropentanamide Step A. (R)-2-(4-Chlorophenylsulfonamido)-5,5,5-trifluoropentanamide

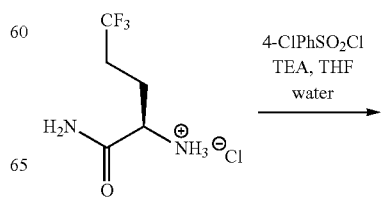

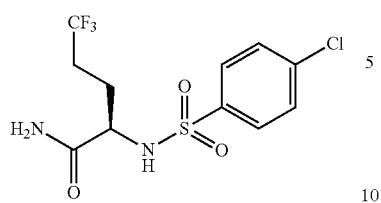

To a suitable dry vessel was added (R)-2-amino-5,5,5-trifluoropentanamide hydrochloride (199.52 g 0.966 mol, 1.0 equiv) followed by 4-chlorobenzenesulfonyl chloride (215.22 g 0.989 mol, 1.02 equiv, 97% w/w %) and 1.6 L of THF at room temperature. Triethylamine (206.5 g, 2.04 mol, 2.1 equiv.) was added over 20 min, maintaining the pot temperature at 15-25° C., and the resulting white slurry was stirred at 15-25° C. for 30 min. Water (1.4 L, 7 vol) of was added to the reaction mixture at 20-25° C. and then THF (1.4 L, 7 vol) was removed by distillation under vacuum (the pot temperature was maintained at 40-60° C. under 250-400 mmHg during distillation process). When the distillation process was complete, 1.4 L (7 vol) of water was added over 30 min while maintaining the pot temperature at 50-60° C., and the resulting slurry was stirred at 50-60° C. for 30 min and then cooled to 10° C. The slurry was agitated for not less than 1 hour, and the product was filtered.

The filter cake was washed with water (600 mL each wash) until the pH of the cake wash measured ≧5. The cake was dried under vacuum at not more than 70° C. (jacket temp.) until the loss on drying is <0.5 w/w %, giving the title compound as a white solid (300 g, 91% yield.) $^1$H NMR (DMSO-$d_6$) (400 MHz) δ 160-1.90 (two m, 1H each of $CH_2$), 2.10-2.35 (m, 2H of $CH_2$—$CF_3$), 3.85-3.88 (m, 1H, ($CONH_2$)CH (NH), 7.13 & 7.37 (br s, 1H, each of $CONH_2$), 7.61 (m, 2H, Ar—$H_a$), 7.64 (m, 2H, Ar—$H_b$), 8.18 (d, 1H, J=8.0 Hz, NH—$SO_2$). $^{13}$C NMR (DMSO-$d_6$) (100.0 MHz) δ 171.75, 140.27, 137.77, 131.71, 129.56, 128.95, 126.22, 55.12, 30.1, 29.82, 29.53, 29.25, 25.82, 25.79.

Step B. (2R)-2-[[(4-Chlorophenyl)sulfonyl][[2-fluoro-4-(1,2,4-oxadiazol-3-yl)phenyl]methyl]amino]-5,5,5-trifluoropentanamide

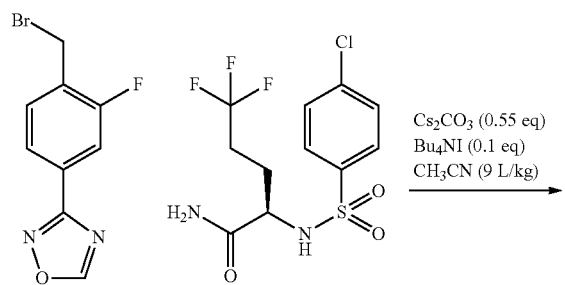

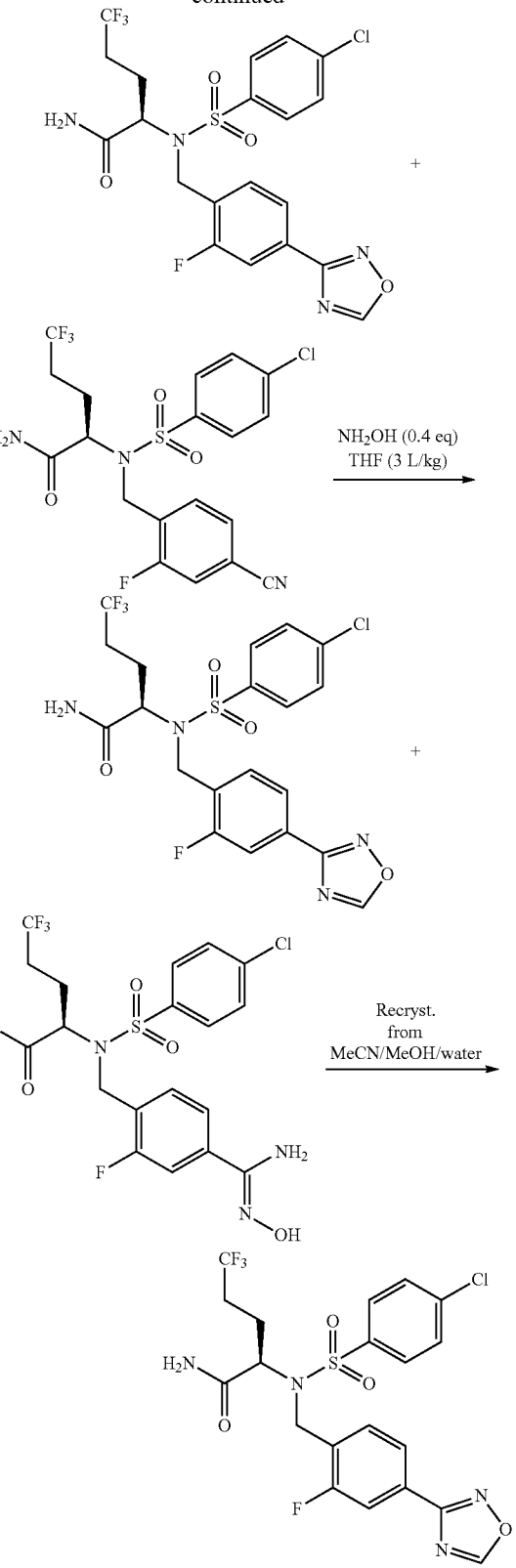

Step B, Procedure 1.

A suitable vessel was charged with 3-(4-(bromomethyl)-3-fluorophenyl)-1,2,4-oxadiazole (492.14 g, 1.10 equiv, 1.914 mol), (R)-2-(4-chlorophenylsulfonamido)-5,5,5-trifluoropentanamide (600 g, 1.00 equiv; 1.74 mol) cesium carbonate (312.22 g, 0.55 equiv; 0.98 mol), tetra-n-butylammonium iodide (64.29 g, 0.10 equiv; 0.17 mmoles), and acetonitrile (9 mL/g; 5.4 L). The jacket was heated to 40° C. (internal 38° C.). The reaction was monitored by HPLC until (R)-2-(4-chlorophenylsulfonamido)-5,5,5-trifluoropentanamide was <5 AP. The vessel was cooled to an internal temperature of 20° C. and water (5.4 L) was added. The phases were separated and the product rich layer was on the top. The bottom layer was discarded. Water (3.7 L) was charged over 18 minutes, and the reaction was held for 20 h at 20° C. and then filtered. Water (6 L) was added to the vessel and agitated to assist in transfer of solid stuck to agitator and vessel walls. The crude cake was washed once with the water used to rinse the reactor. The crude cake was dried in trays under vacuum at 50° C. The dry, crude cake weighed 699 g. The cake was transferred to a 10 L reactor and THF was charged (2.025 L) followed by hydroxylamine solution (50% in water) (42.97 mL, 0.40 equiv, 0.696 mol). The reactor jacket was heated to 40° C. The reaction was monitored by HPLC until (R)-2-(4-chloro-N-(4-cyano-2-fluorobenzyl)phenylsulfonamido)-5,5,5-trifluoropentanamide was <0.4 AP. The reaction was cooled to 20° C., water (2 L) was added and the reaction was stirred at 20° C. for 30 minutes. The phases were separated and the organic phase was treated with heptane (8 L) while stirring and the reaction oiled, then precipitated. The slurry was allowed to stand at 20° C. for 2 h, and the reaction was filtered and the cake was washed with heptane (2 L). The crude cake was tray dried under vacuum at 40-50° C. and weighed 613 g after drying to <1% loss on drying. The crude product was transferred back to the vessel along with MeOH (3.678 L) and MeCN (1.226 L). The jacket was heated to 60° C. (internal 52° C.) to effect complete dissolution, and water (2.023 L) was added at that temperature slowly, maintaining an internal temperature of >50° C. When water addition was complete, the solution was cooled to an internal temperature of 15° C. over 4 hours while crystallization occurred. Additional water was charged to the reactor (400 mL) and the reaction was filtered and the mother liquor was returned to the vessel. The mother liquor was agitated for 2 minutes to free any stuck product in the vessel. The crude cake was washed with mother liquor followed by heptanes (1.500 L). The product was tray dried under vacuum at 40-50° C. until loss on drying was <0.5% to give (2R)-2-[[(4-Chlorophenyl)sulfonyl][[2-fluoro-4-(1,2,4-oxadiazol-3-yl)phenyl]methyl]amino]-5,5,5-trifluoropentanamide as a shiny, off white solid (577.6 g, 63.76% yield.).

Step B, Procedure 2.

To a suitable vessel was added (R)-2-(4-chlorophenylsulfonamido)-5,5,5-trifluoropentanamide (2.68 kg, 7.77 mol, 1 eq), 3-(4-(bromomethyl)-3-fluorophenyl)-1,2,4-oxadiazole (2.00 kg, 7.78 mol, 1 eq), cesium carbonate (1.65 kg, 5.06 mol, 0.65 eq), tetrabutylammonium iodide (0.29 kg, 0.78 mol, 0.1 eq) and acetonitrile (12.0 L 4.5 L/kg). The reaction was heated to 35° C. until complete by HPLC (3-(4-(bromomethyl)-3-fluorophenyl)-1,2,4-oxadiazole <0.5 relative AP by HPLC). The reaction was cooled to 15° C. and water (10.72 L, 4 L/kg) was added with stirring followed by glacial acetic acid (0.22 kg) to bring the pH of the reaction to <6.5. The stirring was stopped and the phases were separated (the top layer contained the product). To the product rich layer was added toluene (26.8 kg, 31 L, 10 kg/kg) followed by brine solution (20% w/w, 6.39 kg, 2 L/kg) and the layers were separated (the top layer contained the product). The mixture was distilled at –50° C. under vacuum (200 mbar) until acetonitrile was removed. The concentration was adjusted with additional toluene if needed after distillation to ensure total volume in the reactor was ~10 L/kg. Isopropyl alcohol (0.48 kg, 0.2 L/kg) was charged and the batch was cooled to 15° C. to initiate crystallization. The resulting slurry was filtered and washed with cold toluene (18.65 kg, 21.56 L, 8 L/kg). The crude cake was tray dried under vacuum at 50° C. until loss on drying was <1.0%. The dry cake was added to a 100 L reactor along with isopropyl alcohol (27.34 kg, 34.8 L, 13 L/kg) and hydroxylamine (50% aqueous solution, 0.05 kg, 1.51 mol, 0.2 eq). The mixture was heated to 65° C. and monitored by HPLC until (R)-2-(4-chloro-N-(4-cyano-2-fluorobenzyl)phenylsulfonamido)-5,5,5-trifluoropentanamide was <0.4 AP. The reaction was then distilled (pot temperature ~50° C., vacuum 300 mbar) until reaction volume was ~60% of original. Acetonitrile (5.36 kg, 2 L/kg) was charged and the reaction temperature was increased to 70° C. to achieve complete dissolution. Water (11.26 L, 4.2 L/kg) was charged slowly while keeping the reaction temperature >65° C. The reaction was cooled to 15° C. over 2 hours and crystallization occurred. The slurry was filtered and washed with cold aqueous isopropyl alcohol (2:1 IPA:water by volume). The cake was dried in a vacuum oven until loss on drying was <1%. The product was then recrystallized by dissolving in acetonitrile (2 L/kg based on weight of input of dried cake) and methanol (6 L/kg) and then heated to 50° C. Water (4 L/kg) was added slowly, keeping the reaction temperature >50° C. The reaction was cooled to 15° C. over 2 hours. The resulting slurry was filtered and washed with a solution of methanol:acetonitrile:water (6:2:4, 5 L/kg) to give (2R)-2-[[(4-chlorophenyl)sulfonyl][[2-fluoro-4-(1,2,4-oxadiazol-3-yl)phenyl]methyl] amino]-5,5,5-trifluoropentanamide (2.02 kg, 50% yield) as a white solid.

EXAMPLE 4

(2R)-2-[[(4-Chlorophenyl)sulfonyl][[2-fluoro-4-(1,2,4-oxadiazol-3-yl)phenyl]methyl]amino]-5,5,5-trifluoropentanamide Step A. (2R)-2-[[(4-Chlorophenyl)sulfonyl][(4-cyano-2-fluorophenyl)methyl]amino]-5,5,5-trifluoropentanamide

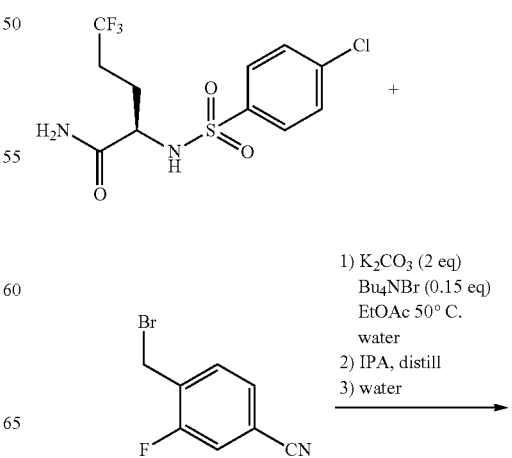

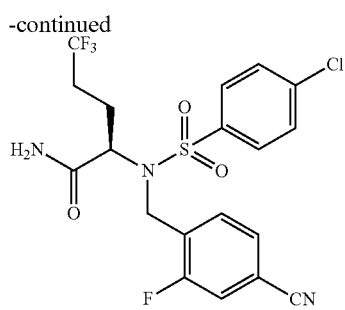

(R)-2-(4-Chlorophenylsulfonamido)-5,5,5-trifluoropentanamide (3.444 kg), potassium carbonate (2.774 kg), tetrabutylammonium bromide (0.484 kg), and 4-(bromomethyl)-3-fluorobenzonitrile (2.092 kg) were charged to a reactor. Ethyl acetate (17.2 L) and water (3.44 L) were then charged and the batch was heated to 50° C. until complete by HPLC (<1 relative AP starting material). The reaction is usually complete in about 15 hours. The batch was cooled to 15-20° C. and water (6.88 L) was charged and the bottom aqueous phase was separated. A solution of sodium phosphate monobasic (0.2 M in water, 20.66 L) was charged and the bottom aqueous phase was separated and the pH was tested to ensure that it was <6.5. (Note: If the pH is >6.5, an additional 20.66 L of 0.2 M sodium phosphate monobasic solution may be charged and the extraction and pH measurement repeated.) The solvent was then exchanged by a constant volume vacuum distillation. The reactor was placed under vacuum (270 mmHg) and the jacket was heated to 75-80° C. Once distillation of ethyl acetate started, isopropanol (41.34 L) was added at the same rate of distillate collection, and the overall batch volume was maintained at a constant level. Once all of the isopropanol was added, the vacuum was released and water (13.76 L) was charged. The batch temperature was maintained at approximately 50° C. during the water addition. The batch was then cooled to 15-20° C. and filtered. The wet cake was washed with 50% (v/v) aqueous isopropanol (4×21.6 kg) and then dried under vacuum at 50° C. to give the title compound as an off-white solid (3.648 kg, 78% yield.) $^1$H NMR (300 MHz, DMSO-$d_6$) δ ppm 1.42-1.55 (m, 1H) 1.80-1.93 (m, 1H) 2.00-2.15 (m, 2H) 4.44 (dd, J=7.91, 1.13 Hz, 1H) 4.68 (d, J=17.71 Hz, 1H) 4.99 (d, J=17.71 Hz, 1H) 7.26 (s, 1H) 7.50 (s, 1H) 7.63-7.73 (m, 4H) 7.78-7.87 (m, 3H). $^{13}$C NMR (75 MHz, DMSO-$d_6$) ppm 22.58-22.97 (m, 1C) 29.96 (d, J=29.09 Hz, 1C) 41.46 (d, J=5.49 Hz, 1C), 57.86, 110.97, 111.45 (d, J=10.43 Hz, 1C), 117.58, 119.11 (d, J=25.80 Hz, 1C), 124.89, 128.53, 128.56, 129.21, 131.17, 131.98, 137.44, 138.32, 158.99 (d, J=247.54 Hz, 2° C.), 170.25. $^{19}$F NMR, (CDCl$_3$, 282 MHz) δ:—116.5, −65.9. IR (KBr): 3443, 3342, 3210, 2955, 2245, 1699, 1577, 1476, 1163 cm$^{-1}$.

Anal, Calcd. for $C_{19}H_{16}ClF_4N_3O_3S$ Calc. C, 47.75; H, 3.37; N, 8.79; S, 6.71; F, 15.90; Cl, 7.41. Found: C, 47.95; H, 3.31; N, 8.67; S, 6.72; F, 15.59; Cl, 7.49.

Step B. (R)-2-(4-Chloro-N-(2-fluoro-4-N'-hydroxycarbamimidoyl)benzyl)phenylsulfonamido)-5,5,5-trifluoropentanamide

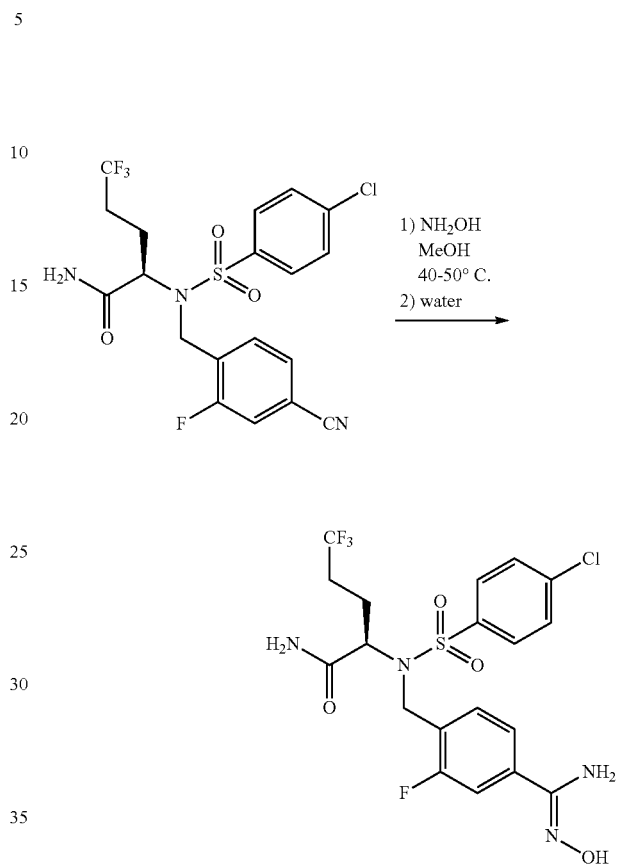

(2R)-2-[[(4-Chlorophenyl)sulfonyl][(4-cyano-2-fluorophenyl)methyl]amino]-5,5,5-trifluoropentanamide (399 g) and methanol (1.6 L) were charged to a reactor followed by hydroxylamine (50% solution in water, 93 mL, 1.8 eq). The mixture was heated to 45-50° C. until complete reaction by HPLC (<0.15 relative AP starting material). Water (0.5 L) was charged slowly, keeping the batch temperature between 30-50° C. The batch was allowed to stand until crystallization started and then water (2.7 L) was charged. The batch was cooled to 15-20° C. and filtered. The cake was washed with 2:1 MeOH:water (2 L) and then dried under vacuum at 50° C. to give the title compound as white solid (415 g, 96% yield). $^1$H NMR (300 MHz, DMSO-$d_6$) δ ppm 1.43-1.64 (m, 1H) 1.77-1.93 (m, 1H) 1.93-2.17 (m, 2H) 4.41 (dd, J=8.48, 6.03 Hz, 1H) 4.60 (d, J=17.14 Hz, 1H) 4.94 (d, J=16.77 Hz, 1H) 5.81-5.98 (m, 2 H) 7.19-7.27 (m, 1H) 7.37-7.47 (m, 2H) 7.52 (d, J=4.14 Hz, 2H) 7.64 (d, J=8.67, Hz, 2H) 7.85 (d, J=8.85 Hz, 2H) 9.71-9.83 (m, 1H). IR (KBr): 3491, 3379, 1680, 1651, 1592, 1433, 1343.

Anal. Calcd. for $C_{19}H_{19}ClF_4N_4O_4S$ Calc. C, 44.66; H, 3.74; N, 10.96; S, 6.27; F, 14.87; Cl, 6.94. Found: C, 44.90; H, 3.91; N, 10.91; S, 6.41; F, 15.21; Cl, 6.95.

Step C. (2R)-2-[[(4-Chlorophenyl)sulfonyl][[2-fluoro-4-(1,2,4-oxadiazol-3-yl)phenyl]methyl]amino]-5,5,5-trifluoropentanamide

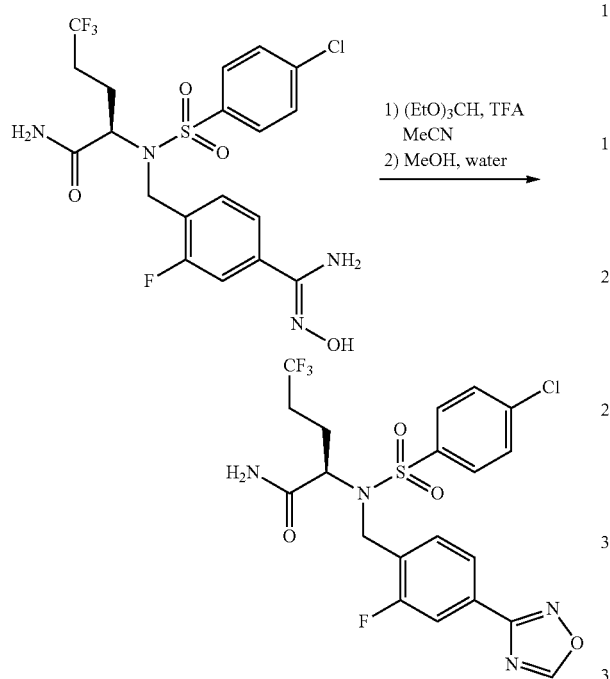

(R)-2-(4-Chloro-N-(2-fluoro-4-(N'-hydroxycarbamimidoyl)benzyl)-phenylsulfonamido)-5,5,5-trifluoropentanamide (246 g) was charged to a reactor followed by dry acetonitrile (509 mL), triethyl orthoformate (120 mL), and trifluoroacetic acid (7 mL). The solution was heated to 40-50° C. until the reaction was complete by HPLC (<0.15 relative AP starting material). Methanol (1.48 L) was charged in one portion, followed by water (1.034 L), keeping the batch at 45-50° C. The batch was then cooled to 15-20° C. and filtered. The cake was washed with 2:6:5 MeCN:MeOH:water and tray dried under vacuum at 50-60° C., giving the title compound as a white solid (228 g, 90% yield). $^1$H NMR, (CDCl$_3$, 300 MHz) δ: 1.40-1.58 (m, 1H) 1.75-1.90 (m, 1H) 1.92-2.07 (m, 1H) 2.10-2.26 (m, 1H) 4.37 (dd, J=8.67, 6.22 Hz, 1H) 4.48 (d, J=15.64 Hz, 1H) 4.64 (d, J=15.82 Hz, 1H) 5.54 (s, 1H) 6.33 (s, 1H) 7.44-7.54 (m, 2H) 7.62 (t, J=7.72 Hz, 1H) 7.68-7.76 (m, 3 H) 7.85 (dd, J=7.91, 1.51 Hz, 1H) 8.76 (s, 1H). $^{13}$C NMR, (DMSO-d$_6$, 75 MHz) δ: 170.34, 167.75, 165.80, 159.64 (d, J=244.5 Hz, 1C), 138.19, 137.64, 131.25 (d, J=3.75 Hz, 1C), 129.31, 129.23, 129.05 (d, J=14.25 Hz, 1C), 126.74 (q, J=274.5 Hz, 1C), 126.91, 126.80, 123.12 (d, J=3.75 Hz, 1C), 113.7 (d, J=24.0 Hz, 1C), 57.92, 41.38 (d, J=4.5 Hz, 1C), 30.04 (d, J=30.0 Hz, 1C), 22.90. $^{19}$F NMR, (CDCl$_3$, 282 MHz) δ:—116.3, −66.5. IR (KBr): 3454, 334, 3286, 2952, 1705, 1432, 1325, 1260, 1167, 1084, 828 cm$^{-1}$.

Anal. Calcd. for $C_{20}H_{17}ClF_4N_4O_4S$ Calc. C, 46.11; H, 3.29; N, 10.71; S, 6.15; F, 14.58; Cl, 6.80. Found C, 46.06; H, 3.24; N, 10.71; S, 6.25; F, 14.60; Cl, 6.88.

What is claimed is:
1. A compound which is

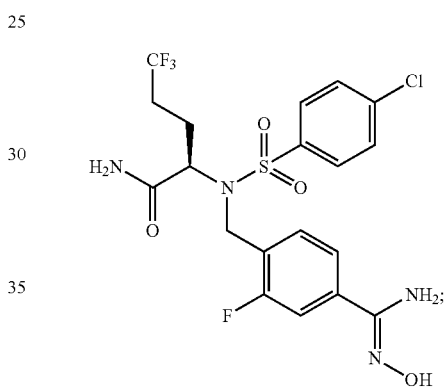

or a pharmaceutically acceptable salt thereof.

* * * * *

UNITED STATES PATENT AND TRADEMARK OFFICE
CERTIFICATE OF CORRECTION

PATENT NO. : 8,350,084 B2  
APPLICATION NO. : 13/299703  
DATED : January 8, 2013  
INVENTOR(S) : Starrett, Jr. et al.

Page 1 of 1

It is certified that error appears in the above-identified patent and that said Letters Patent is hereby corrected as shown below:

On the Title Page:

Item [56], References Cited, under OTHER PUBLICATIONS:

Column 2, Line 29, Selkoe, D.J. reference, delete "Physiological'" and insert -- Physiological --.

Column 2, Line 43, Watkins, T.A. et al. reference, delete "β-Secretase" and insert -- γ-Secretase --.

Signed and Sealed this
Twenty-second Day of April, 2014

Michelle K. Lee
*Deputy Director of the United States Patent and Trademark Office*